United States Patent [19]

Shimizu et al.

[11] 4,436,904
[45] Mar. 13, 1984

[54] CEPHALOSPORINS

[75] Inventors: Shigeo Shimizu; Hiroyuki Takano, both of Yufutsu; Shoji Yoshimura, Iruma; Kinji Takada, Tokyo, all of Japan

[73] Assignee: Kanto Ishi Pharmaceutical Co., Ltd., Tokyo, Japan

[21] Appl. No.: 337,380

[22] Filed: Jan. 6, 1982

[30] Foreign Application Priority Data

Feb. 14, 1981 [JP] Japan .................................. 56-20347
Feb. 14, 1981 [JP] Japan .................................. 56-20348

[51] Int. Cl.³ .................................................. C07D 501/56
[52] U.S. Cl. .................................. 544/27; 544/22; 544/25; 544/28; 548/318
[58] Field of Search ....................... 544/22, 25, 27, 28

[56] References Cited

U.S. PATENT DOCUMENTS 4,200,576 4/1980 Feyen et al. ......................... 544/27
4,291,160 9/1981 Harrison et al. ..................... 544/27

Primary Examiner—Paul M. Coughlan, Jr.
Attorney, Agent, or Firm—Bucknam & Archer

[57] ABSTRACT

Novel cephalosporin derivatives are described which have excellent antibiotic activity against pathogenic bacteria belonging to the Pseudomonas, Serratia and Enterobacter. The compounds have general formula

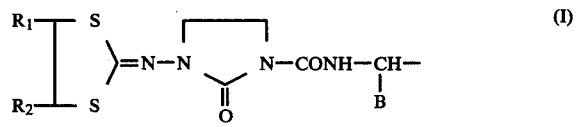

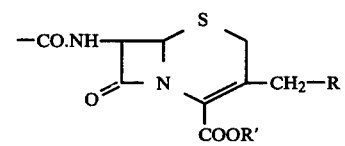

in which R is hydrogen, acyloxy, carbamoyloxy, a substituted or unsubstituted pyridinium group or a group -S-Het in which Het represents a substituted or unsubstituted, hetero atom-containing, 5- or 6-membered heterocyclic ring, R' is hydrogen, alkali metal, an organic amine or an ester moiety, $R_1$ and $R_2$ are the same or different and are hydrogen or a lower alkyl and B stands for a 1,4-cyclohexadienyl group, a group

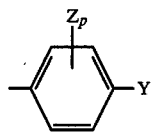

in which Y is hydrogen, —OH or

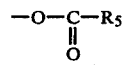

in which $R_5$ is an alkyl of 1 to 5 carbon atoms, aryl or alkoxy having 1 to 4 carbon atoms, Z stands for hydrogen or halogen and p is an integer of 1 or 2, a furan group or a thiophene group. Methods of preparation are described.

11 Claims, No Drawings

CEPHALOSPORINS

BACKGROUND OF THE INVENTION (1) Field of the Invention

The present invention relates to novel cephalosporin derivatives valuable as medicines and processes for the preparation thereof.

More particularly, the present invention relates to novel cephalosporin derivatives having an excellent antibiotic activity against pathogenic bacteria belonging to the general Pseudomonas, Serratia and Enterobacter, and processes for the preparation thereof.

(2) Description of the Prior Art

Japanese Patent Application Laid-Open Specification No. 148795/79 (Richardson-Merrell Incorporated) discloses that a compound represented by the following formula has an excellent antibiotic property:

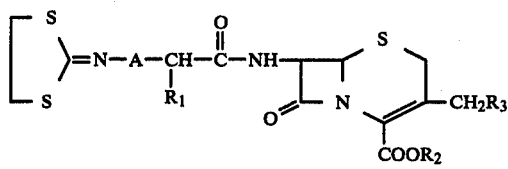

wherein A is selected from the group consisting of sigma bond, phenylene and phenylenethio, $R_1$ is selected from the group consisting of hydrogen, phenyl, amino, hydroxyl, carboxyl and sulfo, $R_2$ is selected from the group consisting of hydrogen, formyloxymethyl and alkanoyloxymethyl (in which the alkanoyl group has 2 to 5 carbon atoms), and $R_3$ is selected from the group consisting of hydrogen, hydroxyl, acetoxy, 5-methyl-1,3,4-thiadiazol-2-yl-thio, 1-methyl-1,2,3,4-tetrazol-5-yl-thio and 1,2,3-triazol-4-yl-thio.

It is suggested by the above laid-open specification that when a 1,3-dithiolan-2-imino group is introduced into a known cephalosporin compound, the antibiotic activity against gram-negative bacteria and gram-positive bacteria is enhanced.

The compound disclosed in the above laid-open specification is very low in effect in the curing of infectious diseases caused by, Pseudomonas, Serratia and Enterobacter, which are now regarded as being difficult to cure.

A series of cephalosporin compounds are disclosed in Japanese Patent Application Laid-Open Specifications Nos. 82286/76, 110592/76, 15398/78, 79895/78 and 39091/79 (all filed by Bayer A. G.), but cephalosporin compounds having a 1,3-dithiolan-2-imino group are not disclosed in any of these laid-open specifications.

SUMMARY OF THE INVENTION

In accordance with one fundamental aspect of the present invention, there is provided a novel cephalosporin represented by the following formula:

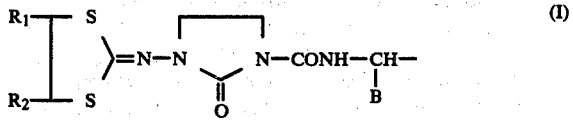

-continued

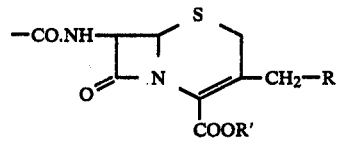

wherein R represents a hydrogen atom, an acyloxy group, a carbamoyloxy group, a substituted or unsubstituted pyridinium group or a group —S—Het in which Het represents a substituted or unsubstituted, hetero atom-containing, a 5- or 6-membered heterocyclic group, R' stands for a hydrogen atom, an alkali metal, an organic amine or an ester moiety, $R_1$ and $R_2$, which may be the same or different, stand for a hydrogen atom or a lower alkyl group, and B stands for a 1,4-cyclohexadienyl group, a group

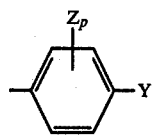

in which Y stands for a hydrogen atom, a group —OH or a group

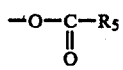

in which $R_5$ represents an alkyl group having 1 to 5 carbon atoms, an aryl group or an alkoxy group having 1 L to 4 carbon atoms, Z stands for a hydrogen or halogen atom and p is an integer of 1 or 2, a furan group or a thiophene group.

In accordance with another aspect of the present invention, there is provided a process for the preparation of novel cephalosporins represented by the above formula (I), which comprises reacting a compound (II) represented by the following formula:

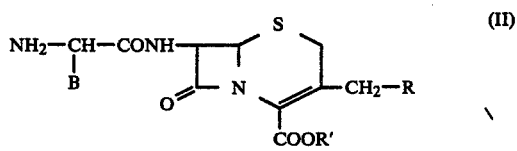

wherein B, R and R' are as defined above, with a reactive derivative of a compound (III) represented by the following formula:

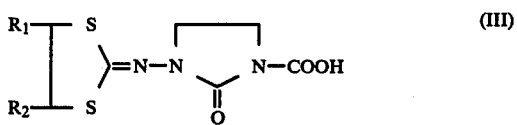

wherein $R_1$ and $R_2$ are as defined above, and, if necessary, acylating or esterifying the resulting reaction product.

In accordance with still another aspect of the present invention, there is provided a process for the preparation of novel cephalosporins represented by the above formula (I), which comprises reacting a compound (IV) represented by the following formula:

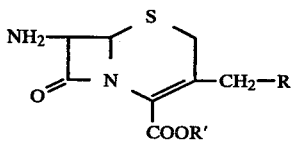

wherein R and R' are as defined above,
with a compound (V) represented by the following formula:

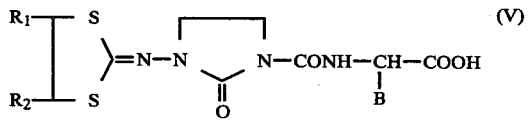

wherein B, R₁ and R₂ are as defined above,
or a reactive derivative thereof, and, if necessary, acylating or esterifying the resulting reaction product.

In accordance with a further aspect of the present invention, there is provided a process for the preparation of novel cephalosporins represented by the above formula (I), which comprises reacting a compound (VI) represented by the following formula:

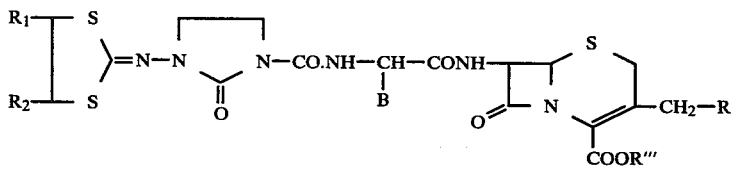

wherein R'' stands for an acyloxy group, R''' stands for a hydrogen atom, an alkali metal or an ammonium group, and B, R₁ and R₂ are as defined above, with a compound (VII) represented by the following formula:

M—S—Het    (VII)

wherein M stands for a hydrogen atom or an alkali metal, and Het is as defined above,
and, if necessary, acylating or esterifying the resulting reaction product.

In accordance with a still further aspect of the present invention, there is provided a novel intermediate represented by the following formula:

wherein R₁ and R₂ are as defined above,
which is used for the above-mentioned preparation processes.

In accordance with a still further aspect of the present invention, there is provided a reactive derivative of a novel intermediate represented by the following formula:

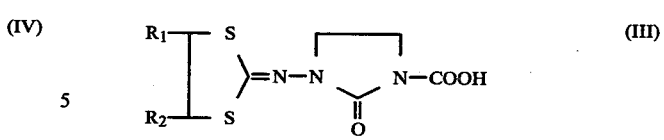

wherein R₁ and R₂ are as defined above,
which is used for the above-mentioned preparation processes.

In accordance with a still further aspect of the present invention, there is provided a compound represented by the following formula or a reactive derivative thereof:

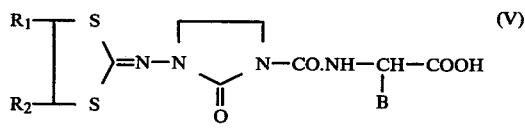

wherein B, R₁ and R₂ are as defined above,
which is used for the above-mentioned preparation processes.

DETAILED DESCRIPTION OF THE PREFERRED EMBODIMENTS

The present invention relates to novel cephalosporin derivatives and processes for the preparation thereof.

More particularly, the present invention relates to novel cephalosporin derivatives having an excellent antibiotic activity against pathogenic bacteria belonging to the genera Pseudomonas, Serratia and Enterobacter, and processes for the preparation thereof.

The intended novel cephalosporin derivatives of the present invention are novel compounds represented by the following formula:

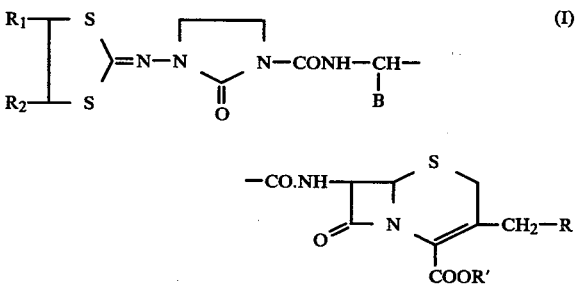

wherein R represents a hydrogen atom, an acyloxy group, a carbamoyloxy group, a substituted or unsubstituted pyridinium group or a group —S—Het in which Het represents a substituted or unsubstituted, hetero atom-containing, a 5- or 6-membered heterocyclic group, R' stands for a hydrogen atom, an alkali metal, an organic amine or an ester moiety, R₁ and R₂, which may be the same or different, stand for a hydrogen atom or a lower alkyl group, and B stands for a 1,4-cyclohexadienyl group or a group

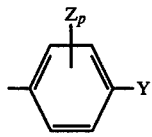

in which Y stands for a hydrogen atom, a group —OH, a group

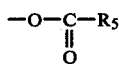

in which $R_5$ represents an alkyl group having 1 to 5 carbon atoms, an aryl group or an alkoxy group having 1 to 4 carbon atoms, Z stands for a hydrogen or halogen atom and p is an integer or 1 or 2, a furan group or a thiohene group. Pharmaceutically acceptable salts, hydrates and organic solvent solvated products of the foregoing compounds are naturally included within the technical scope of the present invention.

The individual groups generally shown in the formula (I) will now be described in detail.

Group R

By the acyloxy group as R is meant a group $R_4$—CO—O— in which $R_4$ stands for an alkyl group having 1 to 4 carbon atoms or a substituted or unsubstituted aryl group. A compound of the formula (I) in which $R_4$ is methyl group is especially preferred because 7-ACA used for the preparation of this compound is easily commercially available and the antibiotic activity of this compound is especially excellent.

By the substituted pyridinium group as R is meant a group

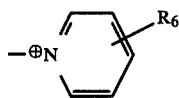

wherein $R_6$ stands for a hydrogen atom, a lower alkyl group, a carboxyl group, a lower alkoxy group, a carbamoyl group, a halogen atom or a sulfamoyl group.

By the group —S—Het as R, there can be mentioned, for example, the following groups:

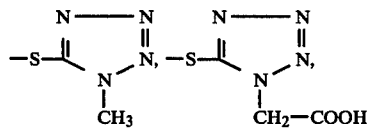

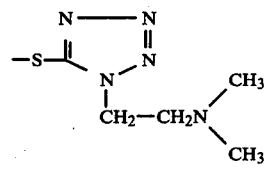

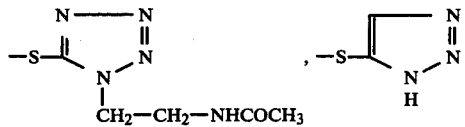

-continued

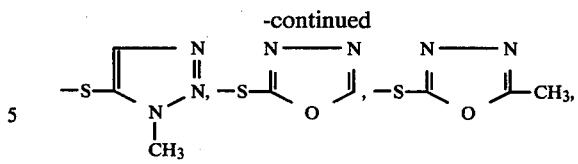

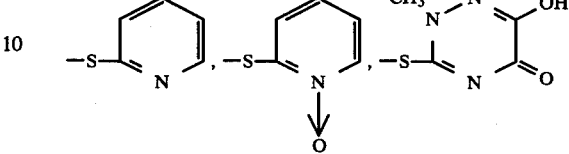

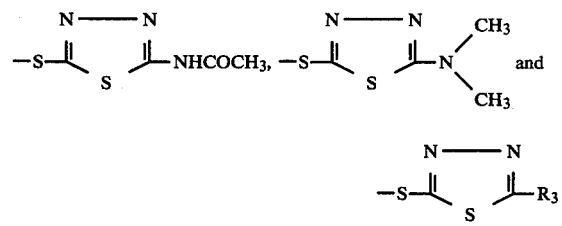
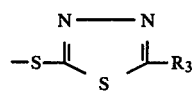

Namely, as is apparent from the above formulae, Het represents a substituted or unsubstituted, hetero atom-containing, 5- or 6-membered heterocyclic group. Incidentally, $R_3$ stands for a hydrogen atom or a lower alkyl group having 1 to 4 carbon atoms.

Group R'

The group R' is explained as the group —COOR'. Namely, as the group —COOR', there can be mentioned a free carboxyl group, salts thereof with alkali metals such as sodium and potassium, salts thereof with organic amines such as triethylamine, diisopropylamine and dicyclohexylamine, and methyl, ethyl, benzyl, acetoxymethyl, α-acetoxyethyl, pivaloyloxymethyl, α-ethoxycarbonyloxymethyl, α-methoxycarbonyloxymethyl, α-methoxycarbonyloxyethyl, benzhydryl, 1-indanyl, phthalidyl, dimethylaminoethyl and trimethylsilyl esters thereof.

Groups $R_1$ and $R_2$ $R_1$ and $R_2$ stand for a hydrogen atom or a lower alkyl group having 1 to 4 crbon atoms, which may be branched, such as methyl, ethyl, propyl and butyl groups.

Group B

B stands for a 1,4-cyclohexadienyl group, a furan group or a thiophene groups. Furthermore, B stands for a group represented by the following general formula:

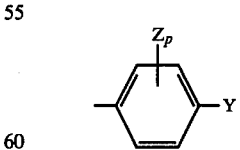

wherein Y stands for a hydrogen atom, a group —OH or a group

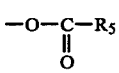

in which $R_5$ is an alkyl group having 1 to 5 carbon atoms, an aryl group or an alkoxy group having 1 to 4 carbon atoms, Z stands for a hydrogen or halogen atom and p is an integer of 1 or 2.

As specific examples, there can be mentioned a p-hydroxyphenyl group and a 4-hydroxy-3-chlorophenyl group, and acyl esters thereof, such as acetic acid, propionic acid, butyric acid, caproic acid, benzoic acid, methylcarbonic acid, propylcarbonic acid and butylcarbonic acid esters.

Processes for Preparation of Novel Cephalosporins

The intended novel cephalosporin derivatives of the present invention are generally prepared according to the following three processes.

First Process

The intended derivatives can be prepared by reacting a compound represented by the following formula:

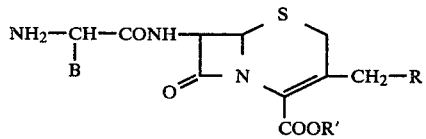
(II)

wherein R, R' and B are as defined above,
with a compound (III) represented by the following formula:

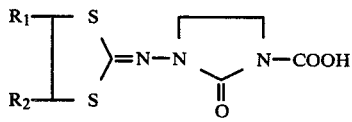
(III)

wherein $R_1$ and $R_2$ are as defined above,
or a reactive derivative thereof.

In the case where B is a p-hydroxyphenyl group (Y=—OH) or R' is a hydrogen atom (R'=H), acylation or esterification of the obtained reaction product is carried out if necessary.

The compound (III) which is used as the starting compound may be obtained by preparing from a compound of the following formula:

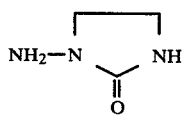

a compound represented by the following formula:

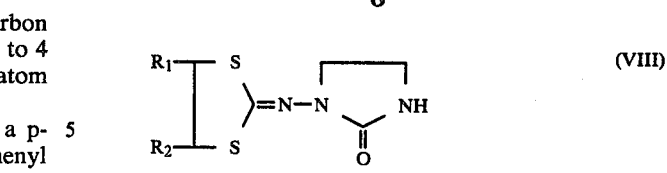
(VIII)

wherein $R_1$ and $R_2$ are as defined above,
silylating the compound (VIII) and subjecting the silylated product chlorocarbonylation with phosgene or trichloromethyl chloroformate.

Second Process

The intended derivatives can be prepared by reacting a compound (IV) represented by the following formula:

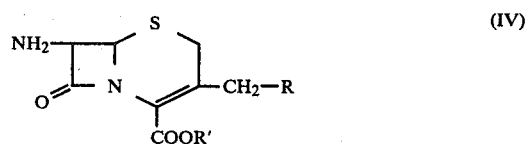
(IV)

wherein R and R' are as defined above,
with a compound (V) represented by the following formula:

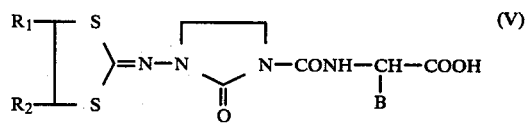
(V)

wherein $R_1$, $R_2$ and B are as defined above.

Acylation or esterification is carried out, if necessary, as described above with respect to the first process.

The compound (V) may be obtained by reacting a reactive derivative of the above-mentioned compound (III) with a compound (X) represented by the following formula:

(X)

wherein B is as defined above.

Third Process

The intended derivatives can be prepared by reacting a compound (VI) represented by the following formula:

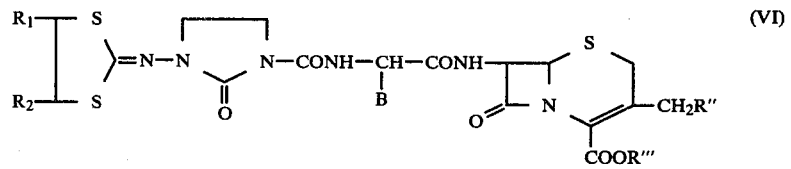
(VI)

wherein $R_1$, $R_2$ and B are as defined above, R" stands for an acyloxy group and R'" stands for a hydrogen atom, an alkali metal or an ammonium group,
with a compound (VII) represented by the following formula:

(VII)

wherein Het is as defined above and M stands for a hydrogen atom or alkali metal.

A compound (I') represented by the following formula:

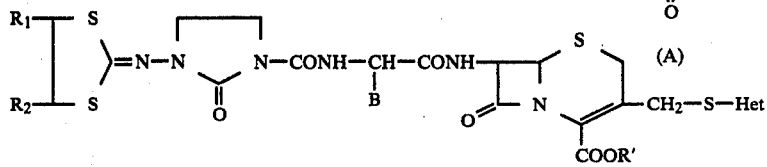

can be prepared by subjecting the resulting compound to acylation or esterification, if necessary, in the same manner as described above with respect to the first process.

The processes for the preparation of the novel cephalosporin derivatives will now be described in detail while referring to novel intermediates used for these preparation processes.

The starting compound (A) can easily be prepared, for example, by subjecting 1-benzalimino-2-oxo-imidazolidone (B) to steam distillation under a sulfuric acid-acidified condition according to customary procedures.

The process is represented by the following reaction formula:

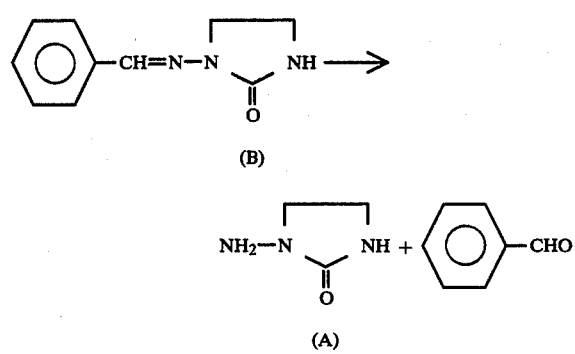

Isolation and purification of the compound (A) may be performed according to customary procedures.

The starting compound (VIII) that is used in the present invention is a novel compound, and this compound can be synthesized according to the following three processes.

Process (a):    (VIII)

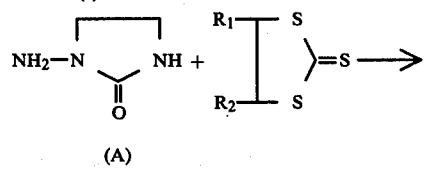

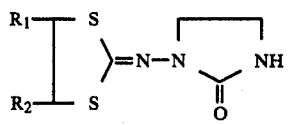

Process (b):    (VIII)

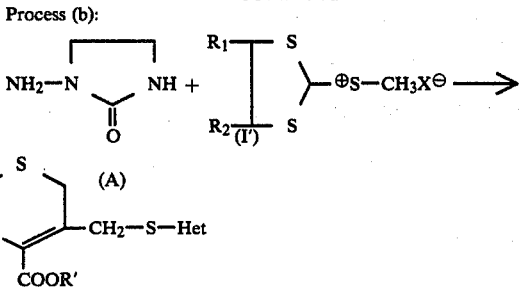

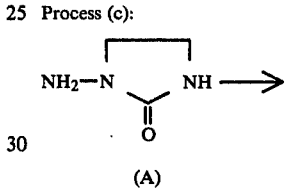

(VIII)

Process (c):

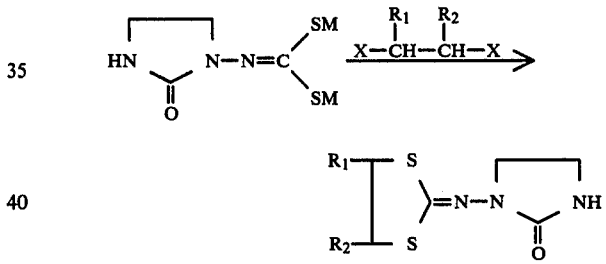

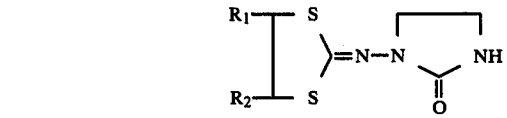

In the above reaction formulae, $R_1$ and $R_2$ are as defined above, $X^\ominus$ stands for a halogen ion, M stands for sodium or potassium, and X stands for a halogen atom.

According to the process (a), the compound (A) is mixed with 1,3-dithiolan-2-thione or a derivative thereof at a substantially equimolar ratio in the absence of a solvent, the mixture is heated at 80° to 150° C. until generation of hydrogen sulfide is stopped, and the reaction product is purified according to customary procedures.

According to the process (b), S-methyl-1,3-dithiolan-2-thione halide (iodide) or its derivative obtained by reacting 1,3-dithiolan-2-thione or its derivative with an alkyl halide, ordinarily methyl iodide, is reacted with the compound (A) at −10° to 80° C., preferably −5° to 30° C., in the presence of a tertiary amine such as triethylamine in an appropriate organic solvent such as methanol, ethanol, dimethylformamide, dimethylacetamide or acetonitrile, completion of the reaction is confirmed by thin layer chromatography and the reaction product is isolated and purified according to customary procedures.

In the above reaction, S-methyl-1,3-dithiolan-2-thione halide (iodide) or its derivative is used in an amount of about 1.0 to about 1.5 moles per mole of the compound (A), preferably in an equimolar amount to the compound (A), and the tertiary amine is used in an amount of about 2 moles per mole of the compound (A).

According to the process (c), at first, the compound (A) is reacted with carbon disulfide at −10° to 50° C. in the presence of an alkali metal hydroxide for about 1 to about 10 hours. In this reaction, the alkali metal hydroxide is used in an amount of about 2 moles per mole of the compound (A). The alkali metal hydroxide may be added at one time at the start of the reaction or it may be added at two times (about one mole at each time). Carbon disulfide is added in an amount of 1 to 3 moles per mole of the compound (A).

Then, the resulting reaction product is reacted with an ethylene halide such as ethylene bromide or ethylene chloride or its derivative in an amount of 1 to 3 moles per mole of the compound (A) at 20° to 100° C., preferably 30° to 35° C., for about 1 to about 10 hours, and the resulting reaction product is isolated and purified according to customary procedures.

A compound (III′) shown below, which is a reactive derivative of the compound (III), is prepared in a high yield with a good quality according to a process represented by the following reaction formula:

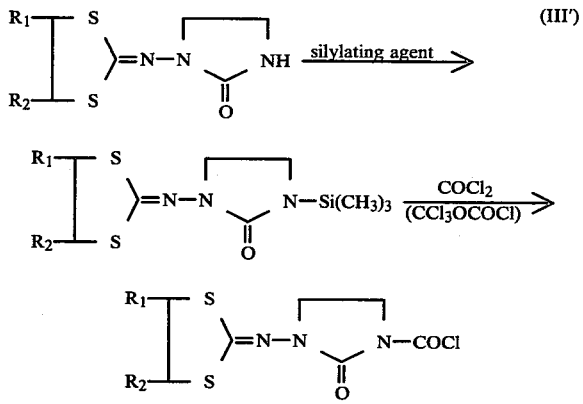

As the silylating agent to be used for this reaction, there are preferably employed trimethylsilyl chloride, hexamethyldisilazane and bistrimethylsilyl acetamide. After the silylation reaction, the reaction product is dissolved in an organic solvent such as tetrahydrofuran, dioxane or dichloromethane and contacted with phosgene or its precursor such as trichloromethyl chloroformate, whereby the novel compound (III′) can easily be obtained.

In this reaction, when phosgene gas is used, reaction is carried out at room temperature for about 2 to about 8 hours by using phosgene gas in an excessive amount over the silylated product of the compound (VIII). When a phosgene precursor is used, reaction is carried out at −25° to 30° C. for about 1 to about 7 hours by using the precursor in an amount of about ½ mole per mole of the silylated product.

The compound (III′) may be purified by recrystallization from an inert organic solvent. According to the above reaction, however, the compound (III′) can be obtained at such a high purity that the as-obtained compound (III′) can conveniently be used directly for the subsequent reaction.

The compound (V) can easily be prepared by reacting the compound (III′) with a substantially equimolar amount of the compound (X) or its silylated derivative in an appropriate solvent in the presence of an deacidifier.

As the solvent that is used for this reaction, there can be mentioned water, tetrahydrofuran, dioxane, acetone, dimethylformamide, dimethylacetamide, acetonitrile, dichloromethane and mixed solvents thereof. The deacidifier is used in a substantially equimolar amount. As the deacidifier, there may be used sodium hydroxide, potassium hydroxide, sodium carbonate, potassium carbonate, triethylamine, pyridine and dimethylaniline. The reaction is carried out at −10° to 50° C. for about 30 minutes to about 2 hours. The so-obtained compound (V) is isolated and purified according to customary procedures.

Some of compounds of the formula (II) are marketed as Cephalexin, Cephaloglycin and derivatives thereof, and other compounds of the formula (II) can be prepared according to known techniques.

Novel cephalosporin derivatives of the present invention can be prepared by using the starting compounds (intermediates) prepared according to the above-mentioned processes.

In the first process, a salt of the compound (II) with, for example, sodium, potassium, triethylamine, pyridine or dimethylaniline or a silylated product of the compound (II) is reacted with the compound (III) or its reactive derivative (III′) at a substantially equimolar ratio in water, ethyl ether, tetrahydrofuran, dioxane, acetone, acetonitrile, dimethylformamide, methylene chloride or a mixed solvent thereof at a low temperature, ordinarily −50° to 30° C., for about 30 minutes to about 3 hours.

The so-obtained product is isolated and purified according to known methods.

In the second process, the compound (V) synthesized according to the above-mentioned process is condensed with a substantially equimolar amount of the compound (IV). It is ordinarily preferred that a reactive derivative of the compound (V) be used. As the reactive derivative, there are used an acid halide, a mixed acid anhydride and an active ester. The free carboxylic acid may be directly used. In this case, it is preferred that an appropriate condensing agent be used in a substantially equimolar amount. As the condensing agent, there can be used N,N′-dicyclohexylcarbodiimide, N,N′-carbonylimidazole, phosphorus oxychloride and Vilsmeier reagent. These condensing agents are well-known reagents used in the fields of chemistry of penicillins, chemistry of cephalosporins and chemistry of peptides.

This reaction is ordinarily carried out in an appropriate solvent such as dichloromethane, chloroform, tetrahydrofuran, dioxane, dimethylformamide, dimethylacetamide, acetonitrile, acetone, dimethylsulfoxide, water or a mixed solvent thereof. The reaction temperature is ordinarily −50° to 30° C., though the reaction temperature changes to some extent according to the kind of the reactive derivative or condensing agent. The reaction time is about 30 minutes to about 3 hours.

The so-obtained compound (I) can easily be isolated and purified according to known methods.

In the third process, the compound (VI) is contacted with the compound (VII) in an amount of 1 to 2 moles per mole of the compound (VI) in water or a mixture of water and water-miscible organic solvent. It is preferred that this reaction be carried out under a substantially neutral condition. When the thiol is used in the free state, the reaction mixture is kept substantially neutral by appropriately adding an alkaline compound such as an alkali metal hydroxide, an alkali metal carbonate, an alkali metal hydrogencarbonate, an alkali metal dihydrogenphosphate or an alkali metal monohydrogenphosphate. The reaction is ordinarily carried out at 20° to 70° C.

Completion of the reaction is confirmed by thin layer chromatography.

Since the obtained compound (I') is dissolved in the form of a water-soluble alkali metal salt in the reaction mixture liquid, if the reaction mixture liquid is made slightly acidic by addition of an acid, the compound (I') is precipitated. The obtained crude product is purified by a method well-known in the art.

In the present invention, if desired, the compounds (I) and (I') prepared according to the above-mentioned first, second and third processes may be acylated according to customary procedures when they have a free hydroxyl group, or they may be converted to pharmaceutically acceptable salts or esters according to customary procedures.

The compounds of the formula (I) prepared according to the present invention have a high antibiotic activity but they have no toxicity at an effective administration dosage (the $LD_{50}$ value is at least 5 g/kg in the intravenous administration to mice). Accordingly, the compounds of the present invention are valuable as medicines. For example, the compounds of the present invention have an excellent antibiotic activity against a variety of pathogenic bacteria such as gram-negative bacteria including Pseudomonas and gram-positive bacteria.

Accordingly, the novel cephalosporin derivatives of the present invention can be effectively utilized for remedy and prevention of various infections diseases caused by the above-mentioned pathogenic bacteria in men and animals.

The cephalosporin derivatives of the present invention can be orally or non-orally administered to men or animals according to various known administration methods.

The derivatives of the present invention may be used singly or in combination with a pharmaceutically acceptable adjuvant, liquid diluent, binder, lubricant or moisture-reserving agent in the form of an ordinary pharmaceutic preparation such as a tablet, granule, sugar-coated tablet, powder, capsule, gel, dry syrup, syrup, ampoule, suspension, liquid, emulsion, ointment, paste, cream or suppository.

As additives that can be incorporated into the derivatives of the present invention, there can be mentioned dissolution-retarding agents, absorption-promoting agents and surface active agents. Namely, in the present invention, there can be used all of known pharmaceutically acceptable additives.

The novel cephalosporin derivatives of the present invention may be used singly or in the form of mixtures of two or more of different derivatives in an amount of about 0.1 to about 99.5% by weight, preferably 0.5 to 95% by weight, based on the total weight of the pharmaceutical composition.

The pharmaceutical composition of the present invention may comprise other pharmaceutically active compounds as effective ingredients in addition to the above-mentioned novel cephalosporin derivative(s).

The daily dose of the novel cephalosporin derivative of the present invention is changed according to the patient or the kind of the animal, the body weight and the disease to be cured, but the daily dose of the cephalosporin derivative is ordinarily in the range of from about 1 to about 1000 mg, preferably about 10 to about 800 mg, per kg of body weight.

The present invention will now be described in detail with reference to the following Examples that by no means limit the scope of the invention.

REFERENCE EXAMPLE 1

Preparation of 1-amino-2-oxo-imidazolidine

A liquid mixture of 208 g of 1-benzalimino-2-oxo-imidazolidine, 2 l of water and 125 ml of concentrated sulfuric acid was subjected to steam distillation for 4 hours, and at this point, distillation of benzaldehyde was substantially stopped. The liquid reaction mixture was filtered and extracted with chloroform. The aqueous solution was neutralized with sodium hydroxide and evaporated to dryness. The residue was extracted with 5 l of chloroform and chloroform was distilled from the chloroform layer. The resulting crude crystal was recrystallized from ethanol to obtain 62 g (the yield being 55%) of the intended compounds. The melting point was 110°–112.5° C.

$^1$H-NMR (CDCl$_3$+d$_6$-DMSO)δ: 3.3–3.5 (4H, m, CH$_2\times$2), 6.44 (2H, broad-s, NH$_2$), 7.97 (1H, broad-s, —NH—)

REFERENCE EXAMPLE 2

Preparation of 1-(1,3-dithiolan-2-imino)-2-oxo-imidazolidine

In 30 ml of water was dissolved 13.6 g of 1-amino-2-oxo-imidazolidine, and a solution of 7.63 g of potassium hydroxide in 10 ml of water was added to the so-formed solution. Then, 12,4 g of carbon disulfide was added dropwise to the mixture over a period of 1 hour. The liquid mixture was stirred for 1 hour at room temperature and for 5 hours at 45° C. Then, excessive carbon disulfide was distilled under reduced pressure, and a solution of 7.63 g of potassium hydroxide in 10 ml of water was added to the residue and the mixture was stirred at room temperature for 30 minutes. Then, 25.6 g of ethylene bromide was added dropwise to the mixture under ice cooling, and the mixture was stirred at room temperature for 10 hours. Water was added to the liquid reaction mixture containing the precipitated crystal and the mixture was heated to form a solution. Petroleum ether was added to the solution to effect washing, and the solution was extracted with chloroform and dried with anhydrous sodium sulfate. The solvent was removed by distillation and the residue was recrystallized from ethyl alcohol to obtain 9.8 g (the yield being 35%) of the intended compound. The melting point was 219°–220° C.

IR (KBr) cm$^{-1}$: $v_{NH}$3260, $v_{C=O}$1690

MS (m/e): 203 (M+)

$^1$H—NMR (CDCl$_3$+d$_6$-DMSO)δ: 3.42 (4H, s,CH$_2\times$2), 3.53 (4H, s, CH$_2\times$2), 6.97 (1H, broad-s, >NH)

Elementary analysis values as C$_6$H$_9$ON$_3$S$_2$: Found value: C=35.71, H=4.45, N=20.43 Calculated value: C=36.00, H=4.50, N=20.70

REFERENTIAL EXAMPLE 3

Preparation of
1-(1,3-dithiolan-2-imino)-2-oxo-imidazolidine

A mixture of 3.03 g of 1-amino-2-oxo-imidazolidine and 3.407 g of 1,3-dithiolan-2-thione was heated and stirred in a nitrogen current on an oil bath maintained at 110° C. for 3 hours. Then, warm water was added to the reaction mixture to form a solution, and the solution was washed with a benzene-hexane mixture and filtered. Water was removed from the filtrate by distillation under reduced pressure and the residue was recrystallized from ethanol to obtain 3.6 g (the yield being 72.5%) of the intended compound. The melting point was 219°–220° C.

REFERENTIAL EXAMPLE 4

Preparation of
1-(1,3-dithiolan-2-imino)-2-oxo-imidazolidine

In 50 ml of dimethylformamide was dissolved 6.46 g of 1-amino-2-oxo-imidazolidine, and 20 ml of triethylamide was added to the solution and the mixture was cooled to −5° C. Then, 19.46 g of S-methyl-1,3-dithiolan-2-thione iodide was added to the solution with stirring over a period of 3 hours. The mixture was stirred at room temperature for 2 hours and dimethylformamide was removed by distillation under reduced pressure. The residue was dissolved in water, washed with benzene and extracted with chloroform. The chloroform layer was dried with anhydrous sodium sulfate and chloroform was removed by distillation. The residue was recrystallized from ethanol to obtain 6.8 g (the yield being 52%) of the intended compound. The melting point was 219°–220° C.

REFERENTIAL EXAMPLE 5

Preparation of
1-(4-methyl-1,3-dithiolan-2-imino)-2-oxo-imidazolidine

In the same manner as described in Referential Example 2, 6.06 g of 1-amino-2-oxo-imidazolidine was reacted with 7.88 g of potassium hydroxide, 6.9 g of carbon disulfide and 12.1 g of 1,2-dibromopropane. The reaction product was purified by silica gel chromatography and recrystallized from benzene to obtain 2.09 g (the yield being 16%) of the intended compound. The melting point was 123°–126° C.

IR (KBr) cm$^{-1}$: $\nu_{NH}$3220, $\nu_{C=O}$1690

$^1$H—NMR (CDCl$_3$+d$_6$-DMSO)δ: 1.50 (3H, t, J=7 Hz, —CH$_3$), 6.60 (1H, s, NH)

REFERENTIAL EXAMPLE 6

Preparation of
1-chlorocarbonyl-2-oxo-3-(1,3-dithiolan-2-imino)-imidazolidine

A mixture of 3.5 g of 1-(1,3-dithiolan-2-imino)-2-oxo-imidazolidine and 7.4 ml of hexamethyldisilazane was heated and refluxed in a nitrogen current for 6 hours, and excessive hexamethyldisilazane was distilled under reduced pressure. Then, 50 ml of tetrahydrofuran was added to the residue to form a solution and phosgene was introduced into the solution at room temperature for 5 hours. The reaction vessel was sealed and the mixture was stirred overnight. The liquid reaction mixture was subjected to distillation under reduced pressure to remove the volatile components completely, whereby 4.89 g of a crude crystal of the intended compound having a melting point of 126° C. was obtained.

REFERENTIAL EXAMPLE 7

Preparation of
1-chlorocarbonyl-2-oxo-3-(1,3-dithiolan-2-imino)-imidazolidine

In 50 ml of dry dichloromethane was suspended 3.0 g (0.015 mole) of 1-(1,3-dithiolan-2-imino)-2-oxo-imidazolidine, and 2.5 ml (0.016 mole) of triethylamine and 2.3 ml (0.016 mole) of trimethylchlorosilane were added to the suspension at room temperature and the mixture was stirred for 1.5 hours. The liquid reaction mixture was cooled to −25° C. and 1 ml (0.0083 mole) of trichloromethyl chloroformate was added to the mixture, and the temperature was elevated to −5° C. over a period of about 1 hour and the mixture was stirred at room temperature for 3 hours. Active carbon was added to the liquid reaction mixture and the mixture was concentrated at 30° C. under reduced pressure. Active carbon was removed by filtration and the filtrate was subjected to distillation under reduced pressure to obtain a light yellow solid. Dry dioxane was added to the obtained solid, insoluble substances were removed by filtration and dioxane was distilled from the resulting solution. A small amount of dichloromethane was added to the resulting light yellow oily product to form a solution and dry ether was added to the solution to obtain 3.1 g (the yield being 78.8%) of a white crystal of 1-chlorocarbonyl-2-oxo-3-(1,3-dithiolan-2-imino)-imidazolidine having a melting point of 126°–127.5° C.

$^1$H—NMR (CDCl$_3$)δ: 3.59 (4H, s, CH$_2$×2), 3.69–4.22 (4H, m, CH$_2$×2)

IR (KBr) cm$^{-1}$: $\nu_{C=O}$1800, 1760, 1700

REFERENTIAL EXAMPLE 8

Preparation of
1-chlorocarbonyl-2-oxo-3-(4-methyl-1,3-dithiolan-2-imino)-imidazolidine A mixture of 2.0 g of 1-(4-methyl-1,3-dithiolan-2-imino)-2-oxo-imidazolidine and 3.88 ml of hexamethyldisilazane was heated and refluxed for 6 hours in a nitrogen current. Then, excessive hexamethyldisilazane was distilled under reduced pressure. Then, 50 ml of tetrahydrofuran was added to the residue to form a solution. Phosgene was introduced into the solution at room temperature for 2 hours. The reaction vessel was sealed and the reaction mixture was stirred overnight. Volatile components were completely distilled from the reaction mixture under reduced pressure to obtain 2.88 g of a viscous crude crystal. This crude crystal was directly used for the next reaction without isolation.

REFERENTIAL EXAMPLE 9

Preparation of
D-(−)-α-{[2-oxo-3-(1,3-dithiolan-2-imino)-imidazolidin-1-yl]-carboxamide}-phenylacetic acid In 10 ml of 2 N sodium hydroxide and 30 ml of water was dissolved 2.57 g of D-(−)-α-phenylglycine, and the pH value was adjusted to 7.6 by addition of 10 ml of 2 N hydrochloric acid to precipitate D-(−)-α-phenylglycine in the finely dispersed state. To the resulting suspension was added 4.89 g of the crude crystal of 1-chlorocarbonyl-2-oxo-3-(1,3-dithiolan-2-imino)-imidazolidine. The pH value was maintained at 7.7 by addition of 2 N sodium hydroxide while the mixture was being stirred. Then, the mixture was filtered, and the filtrate was washed with chloroform and the pH value was adjusted to 2 by addition of 2 N hydrochloric acid under ice cooling to obtain 5.1 g (the yield being 78.9%) of a crystal having a melting point of 227°–230° C.

IR (KBr) cm$^{-1}$: $\nu_{NH}$3325, $\nu_{C=O}$1740, 1650

MS (m/e): 380 (M+)

$^1$H—NMR (d$_6$-DMSO+CDCl$_3$)δ: 3.57 (4H, s, CH$_2$×2), 3.71 (4H, s, CH$_2$×2), 5.37 (1H, d, J=6.8 Hz, α-H), 7.35 (5H, s, phenyl nuclues-H), 8.94 (1H, d, J=6.8 Hz, —CONH)

Elementary analysis values as C$_{15}$H$_{16}$O$_4$N$_4$S$_2$: Calculated: C=47.30, H=4.24, N=14.73; Found: C=46.70, H=4.17, N=14.30

REFERENTIAL EXAMPLE 10

Preparation of D-(−)-α-{[2-oxo-3-(1,3-dithiolan-2-imino)-imidazolidin-1-yl]-carboxyamido}-4-hydroxyphenylacetic acid In 150 ml of dry dichloromethane was suspend 9.2 g of D-(−)-4-hydroxyphenylglycine, and 23.8 ml of triethylamine was added to the suspension. Then, 21.7 ml of trimethylchlorosilane was dropped to the mixture under ice cooling below 10° C. over a period of 15 minutes. The ice bath was removed and the mixture was stirred at room temperature for 1 hour. Then, 16.1 g of the crude crystal of 1-chlorocarbonyl-2-oxo-3-(1,3-dithiolan-2-imino)-imidazolidine was added to the mixture under ice cooling over a period of 10 minutes. The mixture was stirred at room temperature for 4 hours, and 100 ml of water was added and the mixture was stirred to precipitate a crystal. The crystal was removed by filtration, washed with water and dried to obtain 18.71 g (the yield being 94.5%) of the intended compound. The melting point was 230.5°–231.5° C.

IR (KBr) cm$^{-1}$: $\nu_{NH,OH}$3250–3300, $\nu_{C=O}$1720, 1660, 1608

MS (FD) m/e: 396 (M+)

$^1$H—NMR (CDCl$_3$+d$_6$-DMSO)δ: 3.55 (4H, s, CH$_2$×2), 3.69 (4H, s, CH$_2$×2), 5.25 (1H, d, J=7 Hz, C—H), 6.73, 7.20 (4H, d, J=8 Hz, C$_6$H$_4$), 8.78 (1H, d, J=7 Hz, NHCO)

Elementary analysis values as C$_{15}$H$_{16}$N$_4$O$_5$S$_2$: Found: C=45.01, H=4.02, N=14.10, Calculated: C=45.45, H=4.04, N=14.14

EXAMPLE 1

Preparation of 7-{D-(−)-α-[(2-oxo-3-(1,3-dithiolan-2-imino)-imidazolidin-1-yl)-carboxamido]-(1,4-cyclohexadien-1-yl)-acetamido}-3-methyl-3-cephem-4-carboxylic acid In 60 ml of 80% aqueous tetrahydrofuran was suspended 1.837 g of cephaladine hydrate, and 0.607 g of triethylamine was added to the suspension to form a solution. Then, 1.735 g of 1-chlorocarbonyl-2-oxo-3-(1,3-dithiolan-2-imino)-imidazolidine was added little by little to the solution with stirring under ice cooling, and simultaneously, triethylamine was dropped to adjust the pH value to 7.0 to 7.5. Reaction was conducted for 1 hour and 100 ml of water was added to the mixture to adjust the pH value to 7. Tetrahydrofuran was distilled under reduced pressure, and the residue was filtered and 2 N hydrochloric acid was added to the filtrate under ice cooling to adjust the pH value to 2. The precipitated crystal was removed by filtration, washed with water and dried in a vacuum desiccator to obtain 2.585 g (the yield being 89%) of the intended compound. The melting point was 160°–170° C. (decomposition).

IR (KBr) cm$^{-1}$: $c_{=O}$1770 (lactam), 1720, 1675 (COOH, CON<)

NMR (D$_6$-DMSO)δ: 2.02 (3H, s, CH$_3$), 2.4–2.8 (4H, m, cyclohexadiene, nucleus, (CH$_2$×2), 3.20–3.90 (10H, m, CH$_2$×5), 5.04 (1H, d, J=5 Hz, 6-H), 5.45–5.85 (5H, m, 7-H, α-H, cyclohexadiene nucleus, CH×3), 8.50 (1H, d, J=8 Hz, NHCO), 9.16 (1H, d, J=8 Hz, NHCO)

EXAMPLE 2

Preparation of 1-ethoxycarbonyloxyethyl-7-{D-(−)-α-[(2-oxo-3-(1,3-dithiolan-2-imino)-imidazolidin-1-yl)-carboxamido]-(1,4-cyclohexadien-1-yl)-acetamido}-3-methyl-3-cephem-4-carboxylate In 10 ml of dimethylsulfoxide was dissolved 0.81 g of the compound obtained in Example 1, and 0.18 g of potassium carbonate and 0.02 g of 18-Crown-6 (crown ether supplied by Nippon Soda K.K.) were added to the solution and the mixture was stirred at room temperature for 1 hour. Then, 0.32 g of diethyl α-chlorocarbonate was added to the mixture and the mixture was stirred for 4 hours in a nitrogen gas current on a water bath maintained at 35° C. Then, 100 ml of ice water was added to the reaction mixture, and the mixture was extracted with 150 ml of dichloromethane, washed with water two times and dried with anhydrous sodium sulfate. The solvent was removed by distillation to obtain a syrup-like product. The product was dissolved in a small amount of dichloromethane and the solution was dropped into 100 ml of ethyl ether with stirring to effect crystallization. The crystal was recovered by filtration and dried to obtain 0.36 g (the yield being 37%) of the intended compound. The melting point was 124°–128° C. (decomposition).

IR (KBr) cm$^{-1}$: $\nu_{C=O}$1760 (lactam), 1720, 1678 (ester, amide)

$^1$H-NMR (d$_6$-DMSO)δ: 1.22 (3H, t, J=7 Hz, —CH$_2$—CH$_3$), 1.48 (3H, d, J=6 Hz,

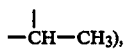

—CH—CH$_3$), 2.03 (3H, s, —CH$_3$), 2.4–2.8 (4H, m, cyclohexadiene nucleus, CH$_2$×2), 3.60 (8H, broad-s, CH$_2$×4), 4.15 (2H, q, J=7 Hz, —CH$_2$—CH$_3$), 4.98 (1H, d, J=5 Hz, 6-H), 5.46–5.83 (5H, m, 7-H, α-H, cyclohexadiene nucleus, CH×3), 6.58–6.90 (1H, m,

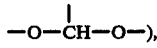

—O—CH—O—), 8.46 (1H, d, J=8 Hz, CONH), 9.13 (1H, d, J=8 Hz, CONH)

EXAMPLE 3

Preparation of 7-{D-(−)-α-[(2-oxo-3-(1,3-dithiolan-2-imino)-imidazolidin-1-yl)-carboxamido]-phenylacetamido}-3-methyl-3-cephem-4-carboxylic acid Reaction was carried out in the same manner as described in Example 1 by using 1.827 g of cephalexin hydrate, 1.593 g of 1-chlorocarbonyl-2-oxo-3-(1,3-dithiolan-2-imino)-imidazolidine and 0.607 g of triethylamine to obtain 2.9 g of the intended compound. The melting point was 162°–170° C. (decomposition).

IR (KBr) cm$^{-1}$: $\nu_{C=O}$1770 (lactam), 1720, 1680 (COOH, CON<)

NMR (d$_6$-DMSO)δ: 2.00 (3H, s, CH$_3$), 3.24, 3.48 (2H, ABq, J=16 Hz, 2-CH$_2$), 3.62 (8H, broad-s, CH$_2$×4), 4.92 (1H, d, J=5 Hz, 6-H), 5.49–5.70 (2H, m, 7-H, α-H), 7.20–7.42 (5H, m, C$_6$H$_5$), 8.84 (1H, d, J=8 Hz, NHCO), 9.37 (1H, d, J=8 Hz, NHCO)

EXAMPLE 4

Preparation of 7-{D-(−)-α-[(2-oxo-3-(1,3-dithiolan-2-imino)-imidazolidin-1-yl)-carboxamido]-4-hydroxyphenylacetamido}-3-[(1,2,3-triazol-5-yl)-thiomethyl]-3-cephem-4-carboxylic acid In 50 ml of dichloromethane was suspended 4.35 g of a methanol adduct of 7-[D-(−)-α-amino-4-hydroxyphenylacetamido]-3-[(1,2,3-triazol-5-yl)-thiomethyl]-3-cephem-4-carboxylic acid, and the suspension was cooled to 0° C. on an ice-sodium chloride bath and 17.2 ml of N,O-bis(trimethylsilyl)acetamide was dropped to the suspension with stirring. After completion of the dropwise addition, the mixture was stirred at room temperature for 2 hours. While the mixture was cooled to −3° C. on an ice-sodium chloride bath, 2.34 g of 1-chlorocarbonyl-2-oxo-3-(1,3-dithiolan-2-imino)-imidazolidine was added. The mixture was stirred at −3° C. for 40 minutes and at room temperature for 2.5 hours. Dichloromethane was distilled under reduced pressure at room temperature, and 300 ml of water was added to the residue and the precipitated crystal was dissolved by addition of 2 N sodium hydroxide. A small amount of active carbon was added to the solution and the mixture was filtered, and the pH value of the precipitate was adjusted to 2 by 2 N hydrochloric acid. The precipitated crystal was recovered by filtration, washed with water and dried in a vacuum desiccator to obtain 4.635 g (the yield being 76%) of the intended compound. The melting point was 177°–186° C. (decomposition). The melting point of the dicyclohexylamine salt of the intended compound was 176° to 182° C. (decomposition).

IR (KBr) cm$^{-1}$: $\nu_{C=O}$1775 (lactam), 1715, 1680 (COOH, CON<)

NMR (d$_6$-DMSO)δ: 3.58 (10H, broad-s, CH$_2$×5), 3.82–4.03 (2H, m, 3-CH$_2$), 4.96 (1H, d, J=5 Hz, 6-H), 5.33–5.80 (2H, m, 7-H, α-H), 6.66, 7.18 (4H, d, J=8 Hz, C$_6$H$_4$—), 7.86 (1H, s, triazole CH), 8.72 (1H, d, J=8 Hz, NHCO), 9.24 (1H, d, J=8 Hz, NHCO)

EXAMPLE 5

Preparation of 7-{D-(−)-α-[(2-oxo-3-(1,3-dithiolan-2-imino)-imidazolidin-1-yl)-carboxamido]-4-acetoxyphenylacetamido}-3-[(1,2,3-triazol-5-yl)-thiomethyl]-3-cephem-4-carboxylic acid To a suspension of 2.075 g of the compound obtained in Example 4 in 25 ml of water was added 6 ml of 1 N sodium hydroxide to form a solution. Then, 0.674 g of acetic anhydride was dropped to the solution with stirring over a period of 20 minutes while the pH value was maintained at 7 to 8 by addition of 1 N sodium hydroxide. The mixture was stirred under ice cooling for 1.5 hours while the pH value was maintained at 7 to 8. The mixture was filtered and the pH value was adjusted to 2 under ice cooling by 2 N hydrochloric acid. The precipitated crystal was recovered by filtration, washed with water and dried in a vacuum desiccator to obtain 1.46 g (the yield being 66%) of the intended compound. The melting point was 166° to 175° C. (decomposition).

IR (KBr) cm$^{-1}$: $\nu_{C=O}$1760 (lactam), 1720, 1685 ester, amide), $\nu_{C-O}$1200

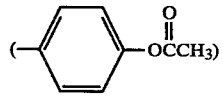

NMR (d$_6$-DMSO)δ: 2.25 (3H, s,

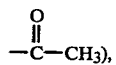

), 3.59 (10H, broad-s, CH$_2$×5), 3.85–4.02 (2H, m, 3-CH$_2$), 4.97 (1H, d, J=5 Hz, 6-H), 5.45–5.78 (2H, m, 7-H, α-H), 7.07, 7.42 (4H, d, J=8 Hz, C$_6$H$_4$—), 7.86 (1H, s, triazole nucleus CH), 8.88 (1H, d, J=8 Hz, NHCO), 9.40 (1H, d, J=8 Hz, NHCO)

EXAMPLE 5b

Preparation of 1-ethoxycarbonyloxyethyl-7-{D-(−)-α-[(2-oxo-3-(1,3-dithiolan-2-imino)-imidazolidin-1-yl)-carboxamide]-4-acetoxyphenylacetamido}-3-[(1,2,3-triazol-5-yl)-thiomethyl]-3-cephem-4-carboxylate In 30 ml of dimethylsulfoxide was dissolved 0.86 g of the compound obtained in Example 5a, and 0.121 g of potassium carbonate and 0.01 g of 18-Crown-6 (crown ether supplied by Nippon Soda K.K.) were added and the mixture was stirred at room temperature for 20 minutes. Then, 0.268 g of diethyl α-chlorocarbonate was added to the mixture and the mixture was stirred in a nitrogen gas current at room temperature for 17 hours and at 30° C. for 9 hours. The reaction mixture was poured into 100 ml of water and extracted with 150 ml of dichloromethane. The extract was washed with water two times and dried with anhydrous sodium sulfate, and the solvent was removed by distillation. The resulting oily residue was purified by silica gel column chromatography (chloroform/ethanol mixture was used as the solvent). The resulting oily product was dissolved in a small amount of dichloromethane and ether was added to the solution to effect crystallization and obtain 0.21 g (the yield being 21%) of the intended compound. The melting point was 105° to 111° C. (decompostion).

IR (KBr) cm$^{-1}$: $\nu_{C=O}$1775, 1760 (lactam), 1720, 1680 (ester, amide), $\nu_{C-O}$1200

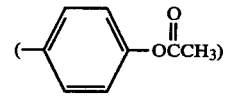

NMR (d$_6$-DMSO)δ: 1.04–1.58 (6H, m, —CH$_2$—C<u>H$_3$</u>,

—CH—CH$_3$), 2.23 (3H, s,

3.58 (10H, s, —CH$_2$×5), 4.13 (2H, g, J=7 Hz, —CH$_2$—CH$_3$), 5.01 (1H, d=5 Hz, 6-H), 5.40–5.74 (2H, m, 7-H, α-H), 7.05, 7.38 (4H, d, J=8 Hz, —C$_6$H$_4$—), 8.15 (1H, s, triazole nucleus CH), 8.86 (1H, d, J=8 Hz, CONH), 9.42 (1H, d, J=8 Hz, CONH)

EXAMPLE 6

Preparation of 7{D-(−)-α-[(2-oxo-3-(4-methyl-1,3-dithiolan-2-imino)-imidazolidin-1-yl)-carboxamido]-phenylacetamido}-3-acetoxymethyl-3-cephem-4-carboxylic acid In 60 ml of 80% aqueous tetrahydrofuran was suspended 2.433 g of cephaloglycin, and 0.607 g of triethylamine was added to the suspension to form a solution. Then, 2.88 g of a crude crystal of 1-chlorocarbonyl-2-oxo-3-(4-methyl-1,3-dithiolan-2-imino)-imidazolidine was added little by little to the solution under ice cooling, and simultaneously, the pH value was maintained at 7.0 to 7.5 by addition of triethylamine. The addition was completed in 30 minutes. Reaction was conducted for 1 hour, and 100 ml of water was added to the reaction mixture and the pH value was adjusted to 7. Tetrahydrofuran was removed by distillation under reduced pressure and the residue was filtered. The pH value of the filtrate was adjusted to 2 under ice cooling by 2 N hydrochloric acid. The precipitated crystal was recovered by filtration, washed with water and dried in a reduced pressure desiccator to obtain 3.75 g (the yield being 96%) of the intended compound. The melting point was 175°–178° C. (decomposition).

IR (KBr) cm$^{-1}$: $\nu_{C=O}$1775 (lactam), 1720, 1700, 1685 (ester carboxylic acid, amide)

$^1$H-NMR (d$_6$-DMSO)δ: 1.45 (3H, d, J=6 Hz, CH—CH$_3$), 2.00 (3H, s,

3.22–3.91 (9H, m, CH$_2$×4,

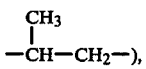

4.61, 4.95 (2H, ABq, J=12 Hz, 3-CH$_2$), 4.96 (1H, d, J=5 Hz, 6-H), 5.50–5.90 (2H, m, 7-H, 6-H), 7.36 (5H, broad-s, C$_6$H$_5$), 8.88 (1H, d, J=8 Hz, CONH), 9.41 (1H, d, J=8 Hz, CONH)

EXAMPLE 7a

Preparation of 7-{D-(−)-α-[(2-oxo-3-(1,3-dithiolan-2-imino)-imidazolidin-1-ly)-carboxamido]-phenylacetamido}-3-acetoxymethyl-3-cephem-4-carboxylic acid In 40 ml of dichloromethane was suspended 3.12 g (0.0077 mole) of anhydrous cephaloglycin, and 2.12 ml of triethylamine was added to the suspension under ice cooling to form a solution. Then, 1.96 ml of trimethylchlorosilane was added to the solution and the mixture was stirred at 15° to 20° C. for 1 hour. Then, 2.0 g (0.0075 mole) of 1-chlorocarbonyl-2-oxo-(1,3-dithiolan-2-imino)-imidazolidine was added to the reaction mixture, and the mixture was stirred at room temperature for 2 hours. Then, 20 ml of water was added and the mixture was stirred for 20 minutes, and the pH value was adjusted to 7 to 8 by a dilute aqueous solution of sodium hydrogen carbonate and the mixture was washed with ethyl acetate. The pH value of the aqueous layer was adjusted to 2 by addition of 4 N HCl. The formed white precipitate was recovered by filtration, washed with water and dried in vacuo to obtain 3.22 g (the yield being 69.4%) of 7-{D-(−)-α-[(2-oxo-3-(1,3-dithiolan-2-imino)-imidazolidin-1-yl-carboxamido]-phenylacetamido}-3-acetoxymethyl-3-cephem-4-carboxylic acid in the form of a white powder having a melting point of 174° to 185° C. (decomposition).

IR (KBr) cm$^{-1}$: $\nu_{C=O}$1780 (lactam)

EXAMPLE 7b

Preparation of dicyclohexylamine salt of 7-{D-(−)-α-[(2-oxo-3-(1,3-dithiolan-2-imino)-imidazolidin-1-yl)-carboxamido]-phenylacetamido}-3-acetoxymethyl-3-cephem-4-carboxylic acid In 20 ml of a liquid mixture of ethyl acetate and ethanol was dissolved 1.1 g of 7-{D-(−)-α-[(2-oxo-3-(1,3-dithiolan-2-imino)-imidazolidin-1-yl)-carboxamido]-phenylacetamido}-3-acetoxymethyl-3-cephem-4-carboxylic acid, and insoluble substances were removed by filtration. Then, 0.88 ml of dicyclohexylamine was added to the solution, and the mixture was concentrated and acetone was added to the concentrate. The mixture was allowed to stand still in a refrigerator, and the formed precipitate was recovered by filtration and washed with acetone to obtain 0.9 g (the yield being 63.8%) of a dicyclohexylamine salt of 7-{D-(−)-α-[(2-oxo-3-(1,3-dithiolan-2-imino)-imidazolidin-1-yl)-carboxamido]-phenylacetamido}-3-acetoxymethyl-3-cephem-4-carboxylic acid in the form of a white crystalline powder having a melting point of 162° to 164° C. (decomposition).

IR (KBr) cm$^{-1}$: $\nu_{C=O}$1780 (lactam)

$^1{}_H$-NMR(CDCl$_3$+d$_6$-DMSO)δ: 0.89–2.38, 2.77–3.41 (m, H of dicyclohexyl group), 1.99 (3H, s, —CH$_3$), 3.30–3.21 (2H, m, 2-CH$_2$), 3.61 (8H, broad-s, CH$_2$×4), 4.91–4.83 (3H, m, —CH$_2$— at 3-position, 6-H), 5.45–5.74 (2H, m, α-H, 7-H), 7.22–7.62 (5H, m, phenyl nucleus H), 8.94 (1H, d, J=7.8 Hz, CONH), 9.36 (1H, J=8.8 Hz, CONH)

D$_2$O-Addedδ: 0.89–2.24, 2.77–3.41 (m, H of dicyclohexyl group), 2.02 (3H, s, —CH$_3$), 3.31–3.21 (2H, m, 2-CH$_2$), 3.62 (8H, s, CH$_2$×4), 4.84–4.90 (3H, m, 3-CH$_2$, 6-H), 5.54–5.64 (2H, m, α-H, 7-H), 7.22–7.26 (5H, m, phenyl nucleus-H)

EXAMPLE 7c

Preparation and purification of sodium 7-{D-(−)-α-[(2-oxo-3-(1,3-dithiolan-2-imino)-imidazolidin-1-yl)-carboxamido]-phenylacetamido}-3-acetoxymethyl-3-cephem-4-carboxylate (hereinafter referred to as KI-6203

In 10 cc of dry dimethylformamide was dissolved 0.5 g of a dicyclohexylamine salt of 7-{D-(−)-α-[(2-oxo-3-(1,3-dithiolan-2-imino)-imidoazolidin-1-yl)-carboxamido]-phenylacetamido}-3-acetoxymethyl-3-cephem-4-carboxylic acid, and 0.8 ml of a 1 M solution of sodium 2-ethylhexanoate in isopropanol was added to the above solution. The mixture was stirred for 5 minutes and dry ether was added to the mixture to form a white precipitate. The precipitate was recovered by filtration, washed with dry ether and dried in vacuo to obtain 0.4 g (the yield being 89.28%) of a dimethylformamide adduct of sodium 7-{D-(—)-α-[(2-oxo-3-(1,3-dithiolan-2-imino)-imidazolidin-1-yl)-carboxamido]-phenylacetamido}-3-acetoxymethyl-3-cephem-4-carboxylate in the form of a white crystalline powder having a melting point of 220° to 222° C. (decomposition).

IR (KBr) cm$^{-1}$: $\nu_{C=O}$1760 (lactam)

In 10 ml of a 1/5 liquid mixture of dry dimethylformamide/methanol was dissolved 1.0 g of the so-obtained dimethylformamide adduct of sodium 7-{D-(—)-α-[(2-oxo-3-(1,3-dithiolan-2-imino)-imidazolidin-1-yl)-carboxamido]-phenylacetamido}-3-acetoxymethyl-3-cephem-4-carboxylate, and the solution was subjected the decoloring treatment with active carbon and a 10% solution of methanol in ether was added to the solution to form a precipitate. The precipitate was recovered by filtration, washed with a liquid mixture of dry methanol and ether and then with dry ether and dried in vacuo to obtain 0.6 g (the yield being 62.5%) of sodium 7-{D-(—)-α-[(2-oxo-3-(1,3-dithiolan-2-imino)-imidazolidin-1-yl)-carboxamido]-phenylacetamido}-3-acetoxymethyl-3-cephem-4-carboxylate in the form of a white crystalline powder having a melting point of 219° to 222° C. (decomposition).

The sodium salt was purified by using Sephadex LH-20 (methanol was used as the developing solvent) to obtain sodium 7-{D-(—)-α-[(2-oxo-3-(1,3-dithiolan-2-imino)-imidazolidin-1-yl)-carboxamido]-phenylacetamido}-3-acetoxymethyl-3-cephem-4-carboxylate in the form of a white crystalline powder having a melting point of 218° to 221° C. (decomposition).

Elementary analysis values as $C_{25}H_{25}N_6O_8S_3Na \cdot 1/2$-$H_2O$: Calculated: C=45.11, H=3.94, N=12.63 Found: C=44.95, H=4.10, N=12.94

IR (KBr) cm$^{-1}$: $\nu_{C=O}$1760 (lactam), 1720, 1680 (amide)

$^1$H-NMR (d$_6$-DMSO)δ: 1.99 (3H, s, —CH$_3$), 3.58 (2H, broad-s, 2-CH$_2$), 3.62 (8H, broad-s, CH$_2 \times 4$), 4.88 (1H, d, J=4.88 Hz, 6-H), 4.87 (2H, s, 3-CH$_2$), 5.40-5.72 (2H, m, 7-H, α-H), 7.36 (5H, broad-s, phenyl-H), 8.90 (1H, d, J=7.32 Hz, CONH), 9.32 (1H, d, J=7.33 Hz, —CONH—)

D$_2$O-Addedδ: 1.99 (3H, s, —CH$_3$), 3.31 (2H, broad-s, 2H, 2-CH$_2$), 3.62 (8H, broad-s, CH$_2 \times 4$), 4.85 (1H, d, J=4.88 Hz, 6-H), 4.85 (2H, s, 3-CH$_2$), 5.53 (1H, d, J=4.88 Hz, 7-H), 5.63 (1H, s, α-H), 7.37 (5H, s, phenyl-H)

$^{13}$C-NMR(d$_6$-$^{12}$C-DMSO)δ: 20.66 (q, —CH$_3$), 25.08 (t, 2-C), 35.99, 44.31 (t, imidazolidine nucleus-CH$_2$), 37.81, 38.85 (t, dithiolan nucleus CH$_2$), 56.01 (d, 6-C), 57.31 (d, α-C), 58.09 (α, 7-C), 64.32 (t, CH$_2$ at 3-position), 113.18 (s, 4-C), 126.57 (d, 2', 6'-phenyl nucleus C), 127.87 (d, 4'-phenyl nucleus C), 128.39 (d, 3', 5'-phenyl nucleus C), 134.24 (s, 3-C), 138.26 (s, 1'-phenyl nucleus C), 151.26 (s, >NCONH—), 155.03 (s, dithiolan nucleus >C=N), 162.95 (s, 8-C), 164.51 (s, COONa), 170.49 (s, imidazolidine nucleus C=O and

181.53 (s, —CONH—)

EXAMPLE 8a

Preparation of 7-{D-(—)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylic acid To a mixture of 1 g of 7-{D-(—)-α-[2-oxo-3-(1,3-dithiolan-2-imino)imidazolidin-1-yl)-carboxamido]-phenylacetamido}-3-acetoxymethyl-3-cephem-4-carboxylic acid and 0.273 g of 5-mercapto-1-methyl-1H-tetrazole was added 50 ml of water, and 1 N sodium hydroxide was added to the mixture to form a solution and adjust the pH value to 6.5. The mixture was heated on an oil bath maintained at 60° C. for 17 hours while introducing nitrogen gas. The pH value was always maintained at 6.5 during the reaction. The reaction mixture was filtered and the pH value was adjusted to 2 under ice cooling by 2 N hydrochloric acid. The precipitated crystal was recovered by filtration, washed with water and dried in a vacuum desiccator. The crystal was dissolved in ethyl acetate under heating and ethyl ether was added to the solution to cause precipitation and obtain 0.55 g (the yield being 50%) of the intended compound. The melting point was 158° to 164° C. (decomposition.)

IR (KBr) cm$^{-1}$: $\nu_{C=O}$1780 (lactam), 1720, 1680 (—COOH, —CON<)

EXAMPLE 8b

Preparation of 7-{D-(—)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylic acid In 10 ml of dry methylene chloride was suspended 1.0 g (0.0026 mole) of D-(—)-α-{[2-oxo-3-(1,3-dithiolan-2-imino)-imidazolidin-1-yl]-carboxamido}-phenylacetic acid, and under ice cooling, 0.366 ml (0.0026 mole) of triethylamine was added to the suspension and 0.317 ml (0.0026 mole) of trimethylchlorosilane was then added. The mixture was stirred at room temperature for 1 hour, and it was cooled to about —20° C. and 0.2 ml (0.0026 mole) of dry dimethylformamide and 0.17 ml (0.0014 mole) of trichloromethyl chloroformate were added. The mixture was stirred at —20° to —15° C. for 4.5 hours.

Separately, 1.3 ml of N,O-bis(trimethylsilyl)acetamide was added to a suspension of 0.86 g (0.0026 mole) of 7-amino-3-[(1-methyl-1,2,3,4-tetrazol-5-yl)-thiomethyl]-3-cephem-4-carboxylic acid in 7 ml of dry methylene chloride, and the mixture was stirred at room temperature for 4 hours. The resulting solution was cooled to —20° C. and added to the above-mentioned chloride-formed solution, and the mixture was stirred at —20° to —15° C. for 1 hour. Then, 16 ml of water was added to the mixture and the mixture was stirred to form a precipitate. When a 10% aqueous solution of sodium hydrogen carbonate was added to adjust the pH value to 7.0, the precipitate was dissolved again. The methylene chloride layer was separated, and the obtained aqueous layer was washed with ethyl acetate. The aqueous layer was subjected to the decoloring treatment with active carbon and 3 N hydrochloric acid was added thereto to adjust the pH value to 2.0. The formed precipitate was recovered by filtration, washed with water and dried in vacuo to obtain 1.28 g (the yield being 70.5%) of 7-{D-(−)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylic acid in the form of a white powder having a melting point of 162° to 169° C. (decomposition).

IR (KBr) cm$^{-1}$: $\nu_{C=O}$ 1780 (lactam)

EXAMPLE 8c

Preparation of dicyclohexylamine salt of 7-{D-(−)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylic acid According to the method described in Example 7b, 1.0 g (the yield being 66.05%) of a dicyclohexylamine salt of 7-{D-(−)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylic acid was prepared in the form of a white crystalline powder having a melting point 158° to 161° C. (decomposition) by using 1.2 g of 7-{D-(−)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylic acid.

IR (KBr) cm$^{-1}$: $\nu_{C=O}$ 1780 (lactam)

$^1$H-NMR(CDCl$_3$+d$_6$-DMSO)δ: 0.94-2.13, 2.79-3.08 (m, H of dicyclohexyl group), 3.45 (2H, broad-s, 2-CH$_2$), 3.60-3.69 (8H, m, CH$_2$×4), 3.92 (3H, s, —CH$_3$), 4.54-4.21 (2H, m, 3-CH$_2$), 4.84 (1H, d, J=4.88 Hz, 6-H), 5.44-5.73 (2H, m, 7-H, α-H), 7.07-7.70 (5H, m, phenyl nucleus H), 8.96 (1H, d, J=7.8 Hz, 1H, —CONH—), 9.34 (1H, d, J=8.03 Hz, —CONH)

D$_2$)-Added δ: 0.94-2.13, 2.79-3.08 (m, H of dicyclohexyl group), 3.44 (2H, broad-s, 2H, 2-CH$_2$), 3.61-3.71 (8H, m, CH$_2$×4), 3.94 (3H, s, CH$_3$), 4.54-4.21 (2H, m, 3-CH$_2$), 4.85 (1H, d, J=4.88 Hz, 6-H), 5.63 (1H, d, J=4.88 Hz, 7-H), 5.64 (1H, s, α-H), 7.08-7.74 (5H, m, phenyl nucleus H)

EXAMPLE 8d

Preparation and purification of sodium 7-{D-(−)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylate (hereinafter referred to as KI-6248)

According to the method described in Example 7c, 2.1 g (the yield being 93.33%) of a dimethylformamide adduct of sodium 7-{D-(−)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylate was prepared in the form of a white crystalline powder having a melting point of 194° to 198° C. (decomposition) by using 2.5 g of a dicyclohexylamine salt of 7-{D-(−)-α-[(2-oxo-3-(1,3-dithilan-2-imino)-imidazolidin-1-yl)-carboxamido]-phenylacetamido}-3-[(1-methyl-1,2,3,4-tetrazol-5-yl)-thiomethyl]-3-cephem-4-carboxylic acid.

IR (KBr) cm$^{-1}$: $\nu_{C=O}$ 1760 (lactam)

In the same manner as described above, 1.4 g (the yield being 73.68%) of sodium 7-{D-(−)-α-[(2-oxo-3-(1,3-dithiolan-2-imino)-imidazolin-1-yl)-carboxamido]-phenylacetamido}-3-[(1-methyl-1,2,3,5-tetrazol-5-yl)-thiomethyl]-3-cephem-4-carboxylate was prepared in the form of a white crystalline powder having a melting point of 196° to 199° C. (decomposition) from 2.1 g of the dimethylformamide adduct of sodium 7-{D-(−)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylate.

IR (KBr) cm$^{-1}$: $\nu_{C=O}$ 1760 (lactam)

The above sodium salt was purified in the same manner as described above to obtain a sodium 7-{D-(−)-α-[(2-oxo-3-(1,2-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylate in the form of a white crystalline powder having a melting point of 198° to 199° C. (decomposition).

Elementary analysis values as C$_{25}$H$_{25}$N$_{10}$O$_6$S$_4$Na.H$_2$O: Calculated: C=41.09, H=3.72, N=19.17 Found: C=41.15, H=4.55, N=19.71

IR (KBr) cm$^{-1}$: $\nu_{C=O}$ 1760 (lactam), 1720, 1610 (amide)

$^1$H-NMR(DMSO-d$_6$)δ: 3.62 (10H, s, CH$_2$×5), 3.91 (3H, s, CH$_3$), 4.33-4.29 (2H, m, 3-CH$_2$), 4.86 (1H, d, J=4.88 Hz, 6-H), 5.70-5.44 (2H, m, 7-H, α-H), 7.36 (5H, broad-s, phenyl nucleus H), 8.91 (1H, d, J=7.81 Hz, CONH), 9.42 (1H, d, J=7.8 Hz, CONH)

D$_2$O-Added δ: 3.58 (10H, broad-s, CH$_2$×5), 3.91 (3H, s, —CH$_3$), 4.33 (2H, m, 3-CH$_2$), 4.85 (1H, d, J=4.88 Hz, 6-H), 5.56 (1H, d, J=4.88 Hz, 7-H), 5.61 (1H, s, α-H), 7.37 (5H, broad-s, phenyl nucleus-H)

$^{13}$C-NMR(d$_6$-$^{12}$C-DMSO)δ: 26.25 (t, 2-C), 33.53 (q, —CH$_3$), 35.99, 44.31 (t, imidazoline nucleus-CH$_2$), 36.65 (t, —CH$_2$S—), 37.81, 38.85 (t, dithiolan nucleus CH$_2$), 56.01 (d, 6-C), 57.18 (d, α-C), 57.96 (d, 7-C), 115.39 (s, 4-C), 126.57 (d, 2', 6', phenyl nucleus C), 127.87 (d, 4'-phenyl nucleus C), 128.39 (d, 3', 5', phenyl nucleus C), 133.46 (s, 3-C), 138.26 (s, 1'-phenyl nucleus C), 151.26 (s, >NCON), 154.51 (s, tetrazole nucleus 5-C), 155.03 (s, dithiolan nucleus C=N), 162.83 (s, 8-C), 164.25 (s, —COONa), 170.23 (s, imidazolidine nucleus C=O), 181.53 (s, —CONH—)

EXAMPLE 9a

Preparation of 7-{D-(−)-α-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylic acid 7-{D-(−)-α-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylic acid was prepared in an amount of 1.20 g (the yield being 67.4%) in the form of a white powder having a melting point of 174° to 179° C. (decomposition) in the same manner as described in Example 8b except that 1.0 g (0.0025 mole) of D-(−)-α-{[2-oxo-3-(1,3-dithiolan-2-imino)-imidazolidin-1-yl]-carboxamido}-4-hydroxyphenylacetic acid and 0.83 g (0.0025 mole) of 7-amino-3-[(1-methyl-1,2,3,4-tetrazol-5-yl)-thiomethyl]-3-cephem-4-carboxylic acid were used and trimethylchlorosilane and triethylamine were used in molar amounts two times the molar amounts used in Example 8b.

IR (KBr) cm$^{-1}$: $\nu_{C=O}$ 1780 (lactam)

EXAMPLE 9b

Preparation of dicyclohexylamine salt of 7-{D-(−)-α-[(2-oxo-3-(1,3-dithiolan-2-imino)-imidazolidin-1-yl)-carboxyamido]-4-hydroxyphenylacetamido}-3-[(1-methyl-1,2,3,4-tetrazol-5-yl)-thiomethyl]-3-cephem-4-carboxylic acid According to the method described in Example 7b, 0.3 g (the yield being 39.63%) of a dicyclohexylamine salt of 7-{D-(—)-α-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylic acid was prepared in the form of a white crystalline powder having a melting point of 167° to 170° C. (decomposition) by using 0.6 g of 7-{D-(—)-α-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylic acid. When acetone was used as the reaction solvent, the intended compound was obtained in a yield of 63.7%.

IR (KBr) cm$^{-1}$: $\nu_{C=O}$ 1770 (lactam)

$^1$H-NMR (CDCl$_3$+d$_6$-DMSO)δ: 0.73–2.34, 2.66–3.28 (m, H of dicyclohexyl group), 3.45 (2H, broad-s, 2-CH$_2$), 3.58–3.74 (8H, m, CH$_2$×4), 3.91 (3H, s, —CH$_3$), 4.20–4.58 (2H, m, 3-CH$_2$), 4.85 (1H, d, J=4.88 Hz, 6-H), 5.37–5.94 (2H, m, 7-H, α-H), 6.73 (2H, d, J=8.3 Hz, 3′, 5′-phenyl nucleus H), 7.37 (2H, d, J=8.3 Hz, 2′, 6′-phenyl nucleus H), 8.69 (1H, d, J=9.28 Hz, —CONH), 8.89 (1H, d, J=6.84 Hz, —CONH)

D$_2$O-Addedδ: 0.73–2.34, 2.66–3.28 (m, H of dicyclohexyl group), 3.45 (2H, broad-s, 2-CH$_2$), 3.57–3.75 (8H, m, CH$_2$×4), 3.89 (3H, s, —CH$_3$), 4.20–4.58 (2H, m, 3-CH$_2$), 4.85 (1H, d, J=4.88 Hz, 6-H), 5.53 (1H, s, α-H), 5.66 (1H, d, J=4.88 Hz, 7-H), 6.78 (2H, d, J=8.78 Hz, 3′, 5′-phenyl nucleus H), 7.27 (2H, d, J=8.78 Hz, 2′, 6′-phenyl nucleus H)

EXAMPLE 9c

Preparation and purification of sodium 7-{D-(—)-α-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylate (hereinafter to as KI-6269)

According to the method described in Example 7c, 0.8 g (the yield being 88.88% of a dimethylformamide adduct of sodium 7-{D-(—)-α-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-cephem-4-carboxylate was prepared in the form of a white crystalline powder having a melting point of 215° to 218° C. (decomposition) by using 1.0 g of a dicyclohexylamine salt of 7-{D-(—)-α-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylic acid.

IR (KBr) cm$^{-1}$: $\nu_{C=O}$ 1760 (lactam)

In the same manner as described above, 1.1 g (the yield being 80.88%) of sodium 7-{D-(—)-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylate was prepared in the form of a white crystalline powder having a melting point of 215° to 218° C. (decomposition) from 1.5 g of the dimethylformamide adduct of sodium 7-{D-(—)-α-[(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylate.

IR (KBr) cm$^{-1}$: $\nu_{C=O}$ 1760 (lactam)

In the same manner as described above, the above sodium salt was purified to obtain sodium 7-{D-(—)-α-[-(2-oxo-3-(1,3-dithiolan-2-imino)-imidazolidin-1-yl)-carboxamido]-4-hydroxyphenylacetamido}-3-[(1-methyl-1,2,3,4-tetrazol-5-yl)-thiomethyl]-3-cephem-4-carboxylate in the form of a white crystalline powder having a melting point of 221° to 222° C. (decomposition).

Elementary analysis values as C$_{25}$H$_{25}$N$_{10}$O$_7$S$_4$.Na.H$_2$O: Calculated: C=40.21, H=3.64, N=18.76; Found: C=40.08, H=3.71, N=19.20

IR (KBr) cm$^{-1}$: $\nu_{C=O}$ 1760 (lactam), 1720, 1680 (amide)

$^1$H-NMR(d$_6$-DMSO)δ: 3.62 (10H, s, CH$_2$×5), 3.91 (3H, s, CH$_3$), 4.06–4.59 (2H, m, 3-CH$_2$), 4.85 (1H, d, J=4.88 Hz, 6-H), 5.29–5.79 (2H, m, 7-H, α-H), 6.71 (2H, d, J=8.3 Hz, 3′, 5′-phenyl nucleus H), 7.19 (2H, d, J=8.3 Hz, 2′, 6′-phenyl nucleus H), 8.76 (1H, d, J=7.81 Hz, —CONH), 9.23 (1H, d, J=6.84 Hz, —CONH), 9.63 (1H, s, phenyl nucleus 4′-OH)

D$_2$O-Addedδ:
3.61 (10H, s, CH$_2$×5), 3.91 (3H, s, —CH$_3$), 4.06–4.57 (2H, m, 3-CH$_2$), 4.84 (1H, d, J=4.88 Hz, 6-H), 5.47 (1H, s, α-H), 5.53 (1H, d, J=4.88 Hz, 7-H), 6.72 (2H, d, J=8.3 Hz, 3′, 5′-phenyl nucleus H), 7.20 (1H, d, J=8.3 Hz, 2′, 6′-phenyl nucleus H)

$^{13}$C-NMR (d$_6$-$^{12}$C-DMSO)δ: 26.25 (t, 2-C), 33.53 (q, —CH$_3$), 35.99, 44.31 (t, imidazolidine nucleus CH$_2$), 36.65 (t, —CH$_2$S), 37.68, 38.85 (t, dithiolan nucleus CH$_2$), 55.49 (d, 6-C), 57.18 (d, α-C), 58.09 (d, 7-C), 115.13 (s, 4-C), 115.13 (d, 3′, 5′-phenyl nucleus C), 127.74 (d, 2′, 6′-phenyl nucleus C), 128.26 (s, 1′-phenyl nucleus C), 133.46 (s, 3-C), 151.26 (s, NHCONH), 154.51 (s, tetrazole nucleus 5-C), 155.03 (s, dithiolan nucleus C=N), 157.11 (s, 4′-phenyl nucleus C), 162.83 (s, 8-C), 164.12 (s, COONa), 170.75 (s, imidazolidine nucleus C=O), 181.41 (s, —CONH)

EXAMPLE 10

Preparation of 7-{D-(—)-α-[(2-oxo-3-(1,3-dithiolan-2-imino)-imidazolidin-1-yl)-carboxamido]-4-acetoxyphenylacetamido}-3-[(1-methyl-1,2,3,4-tetrazol-5-yl)-thiomethyl]-3-cephem-4-carboxylic acid In 50 ml of water was dissolved 3.82 g of the sodium salt obtained in Example 9c, and reaction was carried out in the same manner as described in Example 5a by using 1.07 g of acetic anhydride to obtain 3.17 g (the yield being 81%) of the intended compound. The melting point was 159° to 162° C. (decomposition).

IR (KBr) cm$^{-1}$: $\nu_{C=O}$ 1770 (lactam), 1720, 1680 (COOH, CON<), $\nu_{C=O}$ 1200

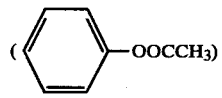

NMR (d$_6$-DMSO)δ: 2.24 (3H, s,

), 3.30–3.80 (10H, broad-s, CH$_2$×5), 3.92 (3H, s, N—CH$_3$), 4.27 (2H, broad-s, 3-CH$_2$), 4.98 (1H, d, J=5 Hz, 6-H), 5.45–5.85 (2H, m, 7-H, α-H), 7.09, 7.43 (4H, d, J=9 Hz, C$_6$H$_4$), 8.91 (1H, d, J=8 Hz, NHCO), 9.44 (1H, d, J=8 Hz, NHCO)

EXAMPLE 11

The minimum inhibitory concentrations (MIC) of the compounds obtained according to the present invention were determined according to the standard method of the Japanese Chemotherapeutic Association.

Cefotiam, cephalexin and cephalothin were used as the control compounds.

The obtained results are shown in Table 1.

Table 1

| Bacteria | Minimum Inhibitory Concentration (MIC) (mcg/ml) Inoculum size: $10^6$ cells/ml | | | | | |
|---|---|---|---|---|---|---|
| | KI-6203 | KI-6248 | KI-6269 | CTM** | CEX** | CET** |
| Gram-Positive Bacteria | | | | | | |
| *Staphylococcus aureus* 209-P | 0.78 | 0.78 | 1.56 | 0.39 | 1.56 | 0.20 |
| *Staphylococcus aureus* TERAJIMA | 1.56 | 0.78 | 1.56 | 0.78 | 1.56 | 0.20 |
| *Staphylococcus epidermidis* ATCC12228 | 0.39 | 0.39 | 0.39 | 0.39 | 1.56 | <0.10 |
| *Bacillus subtilis* ATCC 6633 | 0.78 | 0.78 | 0.78 | 0.39 | 0.78 | <0.10 |
| Gram-Negative Bacteria | | | | | | |
| *Escherichia coli* N I H J | <0.10 | <0.10 | <0.10 | <0.10 | 3.13 | 0.39 |
| *Escherichia coli* MEGAWA | 25 | 6.25 | 6.25 | 6.25 | >100 | >100 |
| *Proteus vulgaris* | 6.25 | 1.56 | 0.78 | 0.39 | 12.5 | 6.25 |
| *Proteus morganii* IID 602 | 6.25 | 3.13 | 3.13 | 0.39 | >100 | >100 |
| *Pseudomonas aeruginosa* IFO 13739 | 12.5 | 12.5 | 6.25 | >100 | >100 | >100 |
| *Pseudomonas aeruginosa* IFO 3080 | 3.13 | 1.56 | 1.56 | >100 | >100 | >100 |
| *Pseudomonas pudita* IID 5121 | 50 | 25 | 25 | >100 | >100 | >100 |
| *Klebsiella pneumoniae* IID 865 | 0.39 | <0.10 | 0.20 | <0.10 | 1.56 | 0.78 |
| *Salmonella enteritidis* IID 604 | 6.25 | 3.13 | 1.56 | 0.20 | 6.25 | 1.56 |
| *Salmonella paratyphi* IID 605 | 6.25 | 1.56 | 1.56 | <0.10 | 12.5 | 3.13 |
| *Salmonella typhimurium* IID 1000 | 3.13 | 0.78 | 1.56 | <0.10 | 3.13 | 0.78 |
| *Shigella boydii* IID 627 | 1.56 | 0.39 | <0.10 | <0.10 | 3.13 | 0.78 |
| *Shigella sonnei* IID 969 | 1.56 | 0.78 | 0.20 | <0.10 | 6.25 | 6.25 |
| *Shigella dysenteriae* IID 633 | 0.78 | 0.20 | <0.10 | <0.10 | 3.13 | 0.78 |
| *Enterobacter aerogenes* IID 5206 | 12.5 | 3.13 | 1.56 | 1.56 | >100 | >100 |
| *Enterobacter cloacae* IID 977 | 12.5 | 3.13 | 3.13 | 3.13 | >100 | >100 |
| *Serratia marcensens* IFO 12648 | 6.25 | 3.13 | 1.56 | 25 | >100 | >100 |

Note
*weight concentration
**potency concentration
CTM: cefotiam
CEX: cephalexin
CET: cephalothin

EXAMPLE 12

Preparation of
7-{D-(—)-α-[(2-oxo-3-(1,3-dithiolan-2-imino)-imidazolidin-1-yl)-carboxamide]-p-hydroxyphenylacetamido}-3-[(1-carboxymethyl-1,2,3,4-tetrazol-5-yl)-thiomethyl]-3-cephem-4-carboxylic acid In 100 ml of dry methylene chloride was suspended 8.721 g (22 millimoles) of D-(—)-α-{[2-oxo-3-(1,3-dithiolan-2-imino)-imidazolidin-1-yl]-carboxamido}-p-hydroxyphenylacetic acid, and 4.452 g (44 millimoles) of triethylamine and 5.019 g (46.2 millimoles) of trimethylchlorosilane were added to the suspension and the mixture was stirred at room temperature for 1 hour. The reaction mixture was cooled to −20° C. and 1.61 g (22 millimoles) of dimethylformamide and 2.39 g (12.1 millimoles) of trichloromethyl chloroformate were added to the reaction mixture. The mixture was stirred at −10° to −15° C. for 5 hours. Separately, 6.679 g (66 millimoles) of triethylamine and 7.684 g (70.4 millimoles) of trimethylchlorosilane were added to a suspension of 8.192 g (22 millimoles) of 7-amino-3-[(1-carboxymethyl-1,2,3,4-tetrazol-5-yl)-thiomethyl]-3-cephem-4-carboxylic acid in 150 ml of dry methylene chloride, and the mixture was stirred at room temperature for 2 hours to form a solution. The solution was cooled to −30° C. and was added to the above chloride-formed solution. The mixture was stirred at −10° to −15° C. for 1 hour, and was then poured into 200 ml of ice water and stirred to cause precipitation. When a 10% aqueous solution of sodium hydrogen carbonate was added to adjust the pH value to 7.0, the precipitate was dissolved again. The methylene chloride layer was separated, and the resulting aqueous layer was washed with ethyl acetate. The aqueous layer was subjected to the decoloring treatment with active carbon and 3 N hydrochloric acid was added thereto to adjust the pH value to 1.5. The resulting precipitate was recovered by filtration, washed with water and dried in vacuo to obtain 13.99 g of a light yellow crude crystal of 7-{D-(—)-α-[(2-oxo-3-(1,3-dithiolan-2-imino)-imidazolidin-1-yl)-carboxamido]-p-hydroxyphenylacetamido}-3-[(1-carboxymethyl-1,2,3,4-tetrazol-5-yl)-thiomethyl]-3-cephem-4-carboxylic acid. The crude crystal was purified by silica gel column chromatography (developing solvent: chloroform/methanol/formic acid=50:10:3→50:15:10) to obtain 7.91 g (the yield being 47.9%) of a purified white crystal having a melting point of 190° C. (decomposition).

IR (KBr) cm$^{-1}$: 1715, 1760–1780 (C=O)

$^1$H-NMR (DMSO-d$_6$)δ: 3.60 (10H, broad-s, CH$_2$×5), 4.20–4.40 (2H, m, 3-CH$_2$), 4.96 (1H, d, J=5 Hz, 6H), 5.20 (2H, s, N—CH$_2$—), 5.43–5.80 (2H, m, 7-H, α-H), 6.72, 7.20 (4H, d, J=8 Hz, —C$_6$H$_4$—), 8.76 (1H, d, J=7.6 Hz, CONH), 9.32 (1H, d, J=7.6 Hz, CONH)

D$_2$O-Added δ: 3.60 (10H, broad-s, CH$_2$×5), 4.20–4.40 (2H, m, 3-CH$_2$—), 4.96 (1H, d, J=5 Hz, 6H), 5.20 (2H, s, N—CH$_2$—), 5.44 (1H, s, α-H), 5.68 (1H, d, J=5 Hz, 7-H), 6.72, 7.20 (4H, d, J=8 Hz, —C$_6$H$_4$—)

EXAMPLE 13a

Preparation of
7-{D-(—)-α-[(2-oxo-3-(1,3-dithiolan-2-imino)-imidazolidin-1-yl)-carboxamido]-phenylacetamido}-3-[(1,3,4-triadiazol-2-yl)-thiomethyl]-3-cephem-4-carboxylic acid In 60 ml of 80% aqueous tetrahydrofuran was suspended 2.31 g of 7-[D-(—)-α-aminophenylacetamido]-3-[(1,3,4-thiadiazol-2-yl)-thiomethyl]-3-cephem-4-carboxylic acid, and 0.607 g of triethylamine was added to the suspension to form a solution. The solution was cooled by ice and 1.593 g of 1-chlorocarbonyl-2-oxo-3-(1,3-dithiolan-2-imino)-imidazolidine was added little by little to the solution with stirring while the pH value was maintained at 7.0 to 7.5 by appropriately adding triethylamine. The addition of the acid chloride was completed within about 30 minutes. The reaction mixture was stirred under ice cooling for 1 hour while the pH value was maintained at 7.0 to 7.5 by addition of triethylamine. Then, 100 ml of water was added to the liquid reaction mixture and the pH value was adjusted to 7, and tetrahydrofuran was distilled under reduced pressure on a water bath maintained at 30° C. The residue was filtered, and the pH value was adjusted to 2 under ice cooling by addition of 2 N HCl. The precipitated crystal was recovered by filtration, washed with water and dried in a vacuum desiccator to obtain 1.73 g of the intended compound. The melting point was 160°–165° C. (decomposition). The yield was 50%.

IR (KBr) cm$^{-1}$: $\nu_{C=O}$ 1780 (lactam)

EXAMPLE 13b

Preparation of 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylic acid In 18 ml of dry methylene chloride was suspended 1.0 g (0.0026 mole) of D-(—)-α-{[2-oxo-3-(1,3-dithiolan-2-imino)-imidazolidin-1-yl]-carboxamido}-phenylacetic acid, and under ice cooling, 0.366 ml (0.0026 mole) or triethylamine was added and 0.317 ml (0.0026 mole) of trimethylchlorosilane was then added. The mixture was stirred at room temperature for 1 hour and cooled to about −20° C., and 0.20 ml (0.0029 mole) of dimethylformamide and 0.17 ml (0.0014 mole) of trichloromethyl chloroformate were added to the mixture. Then, the mixture was stirred at −20° to −15° C. for 4.5 hours. Separately, 1.28 ml of N,O-bis(trimethylsilyl)acetamide was added to a suspension of 0.87 g (0.0026 mole) of 7-amino-3-[(1,3,4-thiadiazol-2-yl)-thiomethyl]-3-cephem-4-carboxylic acid in 7 ml of dry methylene chloride, and the mixture was stirred at room temperature for 4 hours to form a solution. The solution was cooled to −20° C. and added to the above chloride-formed solution, and the mixture was stirred at −20° to −15° C. for 1 hour. Then, 17 ml of water was added to the mixture and the mixture was stirred to form a precipitate. Then, a 10% aqueous solution of sodium hydrogen carbonate was added to adjust the pH value to 7.50 and dissolve the precipitate again. The methylene chloride layer was separated, and the resulting aqueous layer was washed with ethyl acetate and subjected to the decoloring treatment with active carbon. Then, the pH value was adjusted to 2.0 by addition of 3 N hydrochloric acid, and the formed precipitate was recovered by filtration, washed with water and dried in vacuo to obtain 1.25 g (the yield being 68.4%) of 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylic acid in the form of a white powder having a melting point of 164° to 167° C. (decomposition).

IR (KBr) cm$^{-1}$: $\nu_{C=O}$ 1780 (lactam)

EXAMPLE 13c

Preparation of dicyclohexylamine salt of 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylic acid In 20 ml of a liquid mixture of ethyl acetate and ethanol was dissolved 0.8 g of 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylic acid, and insoluble substances were removed by filtration. Then, 0.54 ml of dicyclohexylamine was added to the filtrate, and the mixture was concentrated and acetone was added thereto. The mixture was allowed to stand still in a refrigerator, and the formed precipitate was recovered by filtration and washed with acetone to obtain 0.7 g (the yield being 70%) of a dicyclohexylamine salt of 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylic acid in the form of a white crystalline powder having a melting point of 162° to 165° C. (decomposition).

IR (KBr) cm$^{-1}$: $\nu_{C=O}$ 1780 (lactam)

$^{1}$H-NMR (CDCl$_3$+d$_6$-DMSO)δ: 0.98–2.27, 2.68–3.22 (m, H of dicyclohexyl group), 3.47 (2H, broad-s, 2-CH$_2$), 3.61 (8H, broad-s, CH$_2$×4), 4.49 (2H, broad-s, 3-CH$_2$), 4.87 (1H, d, J=4.88 Hz, 6-H), 5.47–5.72 (2H, m, 7-H, α-H), 7.12–7.67 (5H, m, phenyl nucleus-H), 8.94 (1H, d, J=7.32 Hz, CONH), 9.38 (1H, d, J=7.32 Hz, —CONH), 9.37 (1H, s, thiadiazole nucleus 5-H)

D$_2$O-Addedδ: 0.99–2.27, 2.68–3.22 (m, H of dicyclohexyl group), 3.44 (2H, broad-s, 2-CH$_2$), 3.61 (8H, broad-s, CH$_2$×4), 4.47 (2H, broad-s, 3-CH$_2$), 4.85 (1H, d, J=4.88 Hz, 6-H), 5.59 (1H, d, J=4.88 Hz, 7-H), 5.63 (1H, s, α-H), 7.12–7.67 (5H, m, phenyl nucleus H), 9.34 (1H, s, thiadiazole nucleus 5-H)

EXAMPLE 13d

Preparation and purification of sodium 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylate In 20 cc of dry dimethylformamide was dissolved 2.0 g of a dicyclohexylamine salt of 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylic acid, and 2.96 ml of a 1 M solution of sodium 2-ethylhexanoate in isopropanol was added to the solution and the mixture was stirred for 5 minutes. When dry ether was added to the solution, a white precipitate was formed. The precipitate was recovered by filtration, washed with dry ether and dried in vacuo to obtain 1.7 g (the yield being 94.4%) of a dimethylformamide adduct of sodium 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylate in the form of a white crystalline powder having a melting point of 160°–199° C. (decomposition).

IR (KBr) cm$^{-1}$: $\nu_{C=O}$ 1760 (lactam)

In 10 ml of a 1:5 liquid mixture of dry dimethylformamide:methanol was dissolved 1.7 g of the above dimethylformamide adduct of sodium 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)- thiomethyl]-3-cephem-4-carboxylate, and the solution was subjected to decoloring treatment with active carbon and a dry 10% solution of methanol in ether was added to the solution to form a precipitate. The precipitate was recovered by filtration, washed with a dry liquid mixture of methanol and ether and then with dry ether and dried in vacuo to obtain 1.0 g (the yield being 64.9%) of sodium 7-{D-(−)-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylate in the form of a white crystalline powder having a melting point of 195° to 199° C. (decomposition).

IR (KBr) cm$^{-1}$: $\nu_{C=O}$ 1760 (lactam)

The so-obtained sodium salt was purified by using Sephadex LH-20 (developing solvent: methanol) to obtain sodium 7-{D-(−)-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylate in the form of a white crystalline powder having a melting point of 195° to 202° C. (decomposition).

Elementary analysis values as $C_{25}H_{23}N_8O_6S_5 \cdot Na \cdot H_2O$: Calculated: C=40.97, H=3.44, N=15.29; Found: C=40.84, H=3.43, N=15.53

IR (KBr) cm$^{-1}$: $\nu_{C=O}$ 1760 (lactam), 1710, 1670 (amide)

$^1$H-NMR (d$_6$-DMSO)δ: 3.63 (10H, broad-s, CH$_2$×5), 4.51 (2H, broad-s, 3-CH$_2$), 4.89 (1H, d, J=4.88 Hz, 6-H), 5.52–5.67 (2H, m, 7-H, α-H), 7.37 (5H, s, phenyl nucleus-H), 8.87–8.99 (1H, m, —CONH), 9.52 (1H, s, thiadiazole nucleus 5-H), 9.61–9.35 (1H, m, —CONH)

D$_2$O-Addedδ: 3.61 (10H, broad-s, CH$_2$×5), 4.39–4.48 (2H, m, 3-CH$_2$), 4.86 (1H, d, J=4.88 Hz, 6-H), 5.53 (1H, d, J=4.88 Hz, 7-H), 5.61 (1H, s, α-H), 7.36 (5H, broad-s, phenyl nucleus-H), 9.49 (1H, s, thiadiazole nucleus 5-H)

$^{13}$C-NMR (d$_6$-$^{12}$C-DMSO)δ: 26.51 (t, 2-C), 35.99, 44.31 (t, imidazolidine nucleus CH$_2$), 37.29 (t, —CH$_2$S), 38.85, 37.68 (t, dithiolan nucleus CH$_2$), 56.00 (d, 6-C), 57.31 (d, α-C), 57.96 (d, 7-C), 114.61 (s, 4-C), 126.44 (d, 2', 6'-phenyl nucleus C), 127.74 (d, 4'-phenyl nucleus C), 128.39 (d, 3',5'-phenyl nucleus C), 133.98 (s, 3-C), 138.26 (s, 1'-phenyl nucleus C), 151.26 (s, NCONH), 153.99 (d, thiadiazole nucleus 5-C), 155.03 (s, dithiolan nucleus C=N), 162.70 (s, 8-C), 164.12 (s, —COONa), 166.33 (s, thiadiazole nucleus 2-C), 170.23 (s, imidazolidine nucleus C=O), 181.53 (s, —CONH)

EXAMPLE 14

Preparation of 7-{D-(−)-α-[(2-oxo-3-(1,3-dithiolan-2-imino)-imidazolidin-1-yl)-carboxamido]-phenylacetoamide}-3-[5-methyl-(1,3,4-thiadiazol-2-yl)-thiomethyl]-3-cephem-4-carboxylic acid (hereinafter referred to as TO-180)

To a mixture of 20 ml of anhydrous acetone and 2.66 g of 7-{D-(−)-α-[(2-oxo-3-(1,3-dithiolan-2-imino)-imidazolidin-1-yl]-carboxamido}-phenylacetic acid were added 0.96 ml of triethylamine and one drop of 2-dimethylaminoethanol, and the mixture was cooled to −40° C. and 0.794 g of methyl chloroformate was added thereto. A solution formed by adding 4 ml of 2 N sodium hydroxide to a mixture of 5 ml of water and 2.772 g of 7-amino-3-[5-methyl-(1,3,4-thiadiazol-2-yl)-thiomethyl]-3-cephem-4-carboxylic acid under ice cooling and further adding 7 ml of acetone, which was cooled to −20° C., was added at one time to the above solution, and the mixture was stirred until the temperature was naturally elevated to room temperature. Then, 100 ml of water was added to the mixture, acetone was removed by distillation, and the residue was filtered and the pH value was adjusted to 2 under ice cooling by addition of 2 N hydrochloric acid. The precipitated crystal was recovered by filtration, washed with water and dried in a vacuum desiccator. The crystal was dissolved in ethyl acetate under heating and ethyl ether was added to the solution to precipitate 4.25 g (the yield being 86%) of a crystal of the intended compound having a melting point of 157° to 160° C. (decomposition).

IR (KBr) cm$^{-1}$: $\nu_{C=O}$ 1770 (lactam), 1715, 1675 (COOH, —CON<)

$^1$H-NMR(d$_6$-DMSO)δ: 2.66 (3H, s, —CH$_3$), 3.58 (10H, broad-s, CH$_2$×5), 4.12, 4.44 (2H, ABz, J=12 Hz, 3-CH$_2$), 4.96 (1H, d, J=5 Hz, 6-H), 5.50–5.78 (2H, m, 7-H, α-H), 7.32 (5H, broad-s, C$_6$H$_5$—), 8.84 (1H, d, J=8 Hz, NHCO), 9.40 (1H, d, J=8 Hz, NHCO)

EXAMPLE 15

Preparation of 7-{D-(−)-[(2-oxo-3-(4-methyl-1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylic acid To a mixture of 1.945 g of 7-{D-(−)-α-[(2-oxo-3-(4-methyl-1,3-dithiolan-2-imino)-imidazolidin-1-yl)-carboxamido]-phenylacetamido}-3-acetoxymethyl-3-cephem-4-carboxylic acid, 0.531 g of 5-methyl-2-mercapto-1,3,4-thiadiazole and 60 ml of water was added 1 N sodium hydroxide to form a solution having a pH value of 6.5. The solution was heated and stirred at 60° C. in a nitrogen gas current for 22 hours while maintaining the pH value at 6.5. Then the pH value of the reaction mixture was adjusted to 2 under ice cooling by 2 N hydrochloric acid, and the precipitated crystal was recovered by filtration, washed with water and dried in a vacuum desiccator to obtain 1.895 g (the yield being 89%) of the intended compound. The melting point was 140° to 146° C. (decomposition).

IR (KBr) cm$^{-1}$: $\nu_{C=O}$ 1780 (lactam), 1720, 1680 (—COOH, —CON<)

$^1$H-NMR(d$_6$-DMSO)δ: 1.45 (3H, d, J=6 Hz,

—CH—CH$_3$), 2.65 (2H, s, thiadiazole nucleus CH$_3$), 3.20–3.94 (9H, m, CH$_2$×4,

—CH—CH$_3$), 4.15, 4.50 (2H, ABq, J=13 Hz, 3-CH$_2$), 4.98 (1H, d, J=5 Hz, 6-H), 5.46–5.88 (2H, m, 7-H, α-H), 7.33 (5H, broad-s, C$_6$H$_5$—), 8.88 (1H, d, J=8 Hz, CONH), 9.40 (1H, d, J=8 Hz, CONH)

EXAMPLE 16

The minimum inhibitory concentrations (MIC) of the compound obtained according to the present invention were determined according to the standard method of the Japanese Chemotherapeutic Association.

Cefotiam, cephalexin and cephalothin were used as the control compounds.

The obtained results are shown in Table 2.

TABLE 2

| Bacteria | Minimum Inhibitory Concentration (MIC) (mcg/ml) Inoculum size: $10^6$ cells/ml | | | |
|---|---|---|---|---|
| | TO-180* | CTM** | CEX** | CET** |
| Gram-Positive Bacteria | | | | |
| *Staphylococcus aureus* 209-P | 0.39 | 0.39 | 1.56 | 0.20 |
| *Staphylococcus aureus* TERAJIMA | 0.39 | 0.78 | 1.56 | 0.20 |
| *Staphylcoccus epidermidis* ATCC 12228 | 0.39 | 0.39 | 1.56 | <0.10 |
| *Bacillus subtilis* ATCC 6633 | 0.78 | 0.39 | 0.78 | <0.10 |
| Gram-Negative Bacteria | | | | |
| *Escherichia coli* NIHJ | <0.10 | <0.10 | 3.13 | 0.39 |
| *Escherichia coli* MEGAWA | 6.25 | 6.25 | <100 | <100 |
| *Proteus vulgaris* | 1.56 | 0.39 | 12.5 | 6.25 |
| *Proteus morganii* IID 602 | 1.56 | 0.39 | >100 | >100 |
| *Pseudomonas aeruginosa* IFO 13739 | 6.25 | >100 | >100 | >100 |
| *Pseudomonas aeruginosa* IFO 3080 | 1.56 | >100 | >100 | >100 |
| *Pseudomonas pudita* IID 5121 | 25 | >100 | >100 | >100 |
| *Klebsiella pneumoniae* IID 865 | 0.39 | <0.10 | 1.56 | 0.78 |
| *Salmonella enteritidis* IID 604 | 1.56 | 0.20 | 6.25 | 1.56 |
| *Salmonella paratyphi* IID 605 | 1.56 | <0.10 | 12.5 | 3.13 |
| *Salmonella typhimurium* IID 1000 | 1.56 | <0.10 | 3.13 | 0.78 |
| *Shigella boydii* IID 627 | 0.39 | <0.10 | 3.13 | 0.78 |
| *Shigella sonnei* IID 969 | 0.39 | <0.10 | 6.25 | 6.25 |
| *Shigella dysenteriae* IID 633 | 0.39 | <0.10 | 3.13 | 0.78 |
| *Enterobacter aerogenes* IID 5206 | 3.13 | 1.56 | >100 | >100 |
| *Enterobacter cloacae* IID 977 | 3.13 | 3.13 | >100 | >100 |
| *Serratia marcenscens* IFO 12648 | 1.56 | 25 | >100 | >100 |

Note
*weight concentration
**potency concentration
CTM: cefotiam
CEX: cephalexin
CET: cephalothin

EXAMPLE 17a

Preparation of
7-{D-(—)-α-[(2-oxo-3-(1,3-dithiolan-2-imino)-imidazolidin-1-yl)-carboxamido]-phenylacetamido}{-3-[5-methyl-(1,3,4-thiadiazol-2-yl)-thiomethyl]-3-cephem-4-carboxylic acid According to the method described in Example 13b, 4.11 g (the yield being 76.8%) of 7-{D-(—)-α-[(2-oxo-3-(1,3-dithiolan-2-imino)-imidazolidin-1-yl)-carboxamido]-phenylacetamido}-3-[5-methyl-(1,3,4-thiadiazol-2-yl]-3-cephem-4-carboxylic acid was obtained in the form of a white powder having a melting point of 164° to 165° C. (decomposition) by using 3.0 g (0.00757 mole) of D-(—)-α-{[2-oxo-3-(1,3-dithiolan-2-imino)-imidazolidin-1-yl]-carboxamido}-phenylacetic acid and 2.7 g (0.00762 mole) of 7-amino-3-[(1,3,4-thiadiazol-2-yl)-thiomethyl]-3-cephem-4-carboxylic acid.

IR (KBr) cm$^{-1}$: 1780 (lactam)

EXAMPLE 17b

Preparation of dicyclohexylamine salt of 7-{D-(—)-α-[(2-oxo-3-(1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylic acid In 70 cc of dry acetone was dissolved 1.7 g of 7-{D--(1)-α-[(2-oxo-3-(1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylic acid, and 1.1 ml of dicyclohexylamine was added to the solution and the mixture was allowed to stand still in a refrigerator overnight. The formed precipitate was recovered by filtration and washed with acetone to obtain 1.0 g (the yield being 46.9%) of a dicyclohexylamine salt of 7-{D-(—)-α-[(2-oxo-3-(1,3-dithiolan-2-imino)-imidazolidin-1-yl)-carboxamido]-phenylacetamido}-3-[5-methyl(1,3,4-thiadiazol-2-yl)-thiomethyl]-3-cephem-4-carboxylic acid in the form of a white crystalline powder having a melting point of 162° to 164° C. (decomposition).

IR (KBr) cm$^{-1}$: $\nu_{C=O}$ 1780 (lactam)
$^1$H-NMR(CDCl$_3$+d$_6$-DMSO)δ: 0.79~2.36, 2.85~3.25(m, H of dicyclohexyl group), 2.66(3H, S, —CH$_3$), 3.61 (10H, broad-S, CH$_2$×5), 4.17~4.63(2H, m, 3-CH$_2$), 4.88(1H, d, J=4.88 Hz, 6-H), 5.03~5.90(2H, m, 7-H, α-H), 7.38(5H, broad-S, phenyl nucleus-H), 8.93(1H, d, J=7.81 Hz, CONH), 9.40(1H, d, J=7.33 Hz, —CONH)

D$_2$O-Addedδ: 0.86~2.13, 2.93~3.08(m, H of dicyclohexyl group), 3.62(10H, broad-S, CH$_2$×5), 4.19~4.50(2H, m, 3-CH$_2$), 4.87(1H, d, J=4.88 Hz, 6-H), 5.58(1H, d, J=4.88 Hz, 7-H), 5.64(1H, S, α-H), 7.36(5H, broad-S, phenyl nucleus-H)

EXAMPLE 17c

Preparation and purification of sodium 7-{D-(—)-α-[(2-oxo-3-(1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylate (hereinafter referred to as KI-6271)

According to the method described in Example 13d, 1.5 g (the yield being 83.33%) of a dimethylformamide adduct of sodium 7-{D-(—)-α-[(2-oxo-3-(1,3-dithiolan-2-imino)-imidazolidin-1-yl)-carboxamido]-phenylacetamido}-3-[5-methyl(1,3,4-thiadiazol-2-yl)-thiomethyl]-3-cephem-4-carboxylate was obtained in the form of a white powder having a melting point of 190° to 195° C. (decomposition) by using 2.0 g of a dicyclohexylamine salt of 7-{-D-(—)-α-[(2-oxo-3-(1,3-dithiolan-2-imino)-imidazolidin-1-yl)-carboxamido]-phenylacetamido}-3-[5-methyl(1,3,4-thiadiazol-2-yl)-thiomethyl]-3-cephem-4-carboxylic acid.

IR (KBr) cm$^{-1}$: $\nu_{C=O}$ 1760 (lactam)

In the same manner as described above, 1.1 g (the yield being 80%) of sodium 7-{D-(−)-α-[(2-oxo-3-(1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylate was obtained in the form of a white crystalline powder having a melting point of 194° to 197° C. (decomposition) from 1.5 g of the dimethylformamide adduct of sodium 7-{D-(−)-α-[(2-oxo-3-(1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylate.

IR (KBr) cm$^{-1}$: $\nu_{C=O}$ 1760 (lactam)

In the same manner as described above, the above sodium salt was purified to obtain sodium 7-{D-(−)-α-[(2-oxo-3-(1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylate in the form of a white crystalline powder having a melting point of 194° to 197° C. (decomposition).

Elementary analysis values as $C_{26}H_{25}O_6N_8S_5Na.2-H_2O$: Calculated: C=40.83, H=3.82, N=14.65; Found: C=40.84, H=3.60, N=14.65

IR (KBr) cm$^{-1}$: $\nu_{C=O}$ 1760 (lactam), 1720, 1670 (amide)

$^1$H-NMR(d$_6$-DMSO)δ: 2.66(3H, S, thiadiazole nucleus-CH$_3$), 3.62(10H, broad-S, CH$_2$×5), 4.43(2H, broad-S, 3-CH$_2$), 4.88(1H, d, J=4.88 Hz, 6-H), 5.70~5.45(2H, m, 7-H, α-H), 7.36(5H, S, phenyl nucleus-H), 8.90(1H, d, J=3.32 Hz, —CONH—), 9.39(1H, d, J=8.30 Hz, —CONH—), D$_2$O-Addedδ: 2.66(3H, S, thiadiazole nucleus-CH$_3$), 3.63 (10H, broad-S, —CH$_2$×5), 4.42(2H, broad-S, 3-CH$_2$), 4.86(1H, d, J=4.88 Hz, 6-H), 5.55 (1H, d, J=4.88 Hz, 7-H), 5.62(1H, S, α-H), 7.37(5H, S, phenyl nucleus-H)

$^{13}$C-NMR(d$_6$-$^{12}$C-DMSO)δ: 15.20(q, —CH$_3$), 26.51(t. 2-c), 35.99, 44.31 (t, imidazolidine nucleus), 37.17 (t, —CH$_2$—S), 37.81, 38.85 (t, dithiolan nucleus CH$_2$), 56.01 (d, 6-C), 57.31 (d, α-C), 57.96 (d, 7-C), 115.13(S, 4-C), 126.57(d, 2', 6'-phenyl nucleus), 127.87(d, 4'-phenyl nucleus), 128.39(d, 3', 5'-phenyl nucleus), 133.72(S, 3-C), 138.26(S, 1'-phenyl nucleus), 151.26(S, >N—CO—NH—), 155.03(S, C=N), 162.83(S, 8-C), 164.25(S, —COONa), 165.29(S, 5'-thiadiazole nucleus), 165.94(S, 2'-thiazole nucleus), 170.23(S, imidazolidine nucleus C=O), 181.53(S, —CONH—)

EXAMPLE 17d

Preparation of 1-ethoxycarbonyloxyethyl 7-{D-(−)-α-[(2-oxo-3-(1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylate In 20 ml of dimethylsulfoxide was dissolved 2.12 g of the compound obtained in Example 14, and 0.373 g of potassium carbonate and 0.02 g of 18-Crown-6 (crown ether supplied by Nippon Soda K. K.) were added to the solution and the mixture was stirred at room temperature for 30 minutes. Then, 0.686 g of diethyl α-chlorocarbonate was added to the mixture and the mixture was stirred for 3 hours on a water bath maintained at 50° C. in a nitrogen gas current. Then, 200 ml of ice water was added to the reaction mixture, and the mixture was extracted with 200 ml of dichloromethane, washed with water 2 times and dried was anhydrous sodium sulfate. The solvent was removed by distillation, and 1.84 g of the obtained oily product was dissolved in a small amount of dichloromethane and the solution was dropped into 150 ml of ethyl ether with stirring to effect crystallization. The formed crystal was recovered by filtration and dried to obtain 1.14 g (the yield being 46%) of the intended compound. When the obtained product was purified by silica gel column chromatography (developing solvent: benzene/acetone=2/1), two kinds of oily products were obtained. Each oily product was dissolved in a small amount of dichloromethane and the solution was dropped into ether to effect crystallization. Thus, there were obtained 0.410 g of a steric isomer A in the form of a white powder having a melting point of 125° to 128° C. and 0.230 g of an isomeric isomer B in the form of a white powder having a melting point of 110° to 113° C.

Isomer A (melting point=125°-128° C.)

IR (KBr) cm$^{-1}$: $\nu_{C=O}$ 1760(lactam), 1720, 1680(ester, amide)

$^1$H-NMR (d$_6$-DMSO)δ: 1.23(3H, t, J=8 Hz, —CH$_2$—CH$_3$), 1.55(2H, d, J=6 Hz, —CH—CH$_3$), 2.70(3H, S, Thiadiazole nucleus-CH$_3$), 3.50~3.83(10H, broad-S, CH$_2$×5), 3.93~4.57(4H, m, 3-CH$_2$, —CH$_2$—CH$_3$), 5.06(1H, d, J=5 Hz, 6-H), 5.50~6.00(2H, m, 7-H, α-H), 6.66~7.13(1H, m,

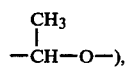

7.20~7.53(5H, m, C$_6$H$_3$—), 8.93(1H, d, J=8 Hz, —NH-CO—), 9.50(1H, d, J=8 Hz, —NHCO—)

Isomer B (melting point=100°-113° C.)

IR (KBr) cm$^{-1}$: $\nu_{C=O}$ 1760(lactam), 1720, 1680(ester, amide)

$^1$H-NMR(DMSO-d$_6$)δ: 1.23(3H, t, J=8 Hz, —CH$_2$—CH$_3$), 1.50(2H, d, J=6 Hz, —CH—CH$_3$), 2.72(3H, S, thiadiazole nucleus-CH$_3$), 3.46~3.83 (10H, broad-S, CH$_2$×5) 4.00~4.37(4H, m, 3-CH$_2$, —CH$_2$—CH$_3$), 4.96~5.33(1H, m, 6-H), 5.47~5.80(2H, m, 7-H, α-H), 6.46~6.90(1H, m,

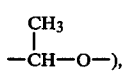

7.16~7.30(5H, m, C$_6$H$_5$—), 8.93(1H, d, J=8 Hz, —NH-CO—), 9.57(1H, d, J=8 Hz, —NHCO—)

EXAMPLE 18a

Preparation of 7-{D-(−)-α-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylic acid 7-{D-(−)-α-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylic acid was prepared in an amount of 4.0 g (the yield being 74.6%) in the form of a white powder having a melting point of 171° to 176° C. (decomposition) in the same manner as described in Example 136 except that 3.0 g (0.0075 mole) of D-(−)-α-{[2-oxo-3-(1,3-dithiolan-2-imino)-imidazolidin-1-yl]-carboxamido}-p-hydroxyphenylacetic acid and 2.49 g (0.0075 mole) of 7-amino-3-[(1,3,4-thiadiazole-2-yl)-thiomethyl]-3-cephem-4-carboxylic acid were used and trimethylchlorosilane and triethylamine were used in molar amounts two times the molar amounts used in Example 13b.

IR (KBr) cm$^{-1}$: $\nu_{C=O}$ 1780 (lactam)

EXAMPLE 18b

Preparation of dicyclohexylamine salt of 7-{D-(—)-α-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylic acid In 250 cc of a liquid mixture of acetone and ethanol was dissolved 4.0 g of 7-{D-(—)-α-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylic acid, and 2.08 ml of dicyclohexylamine was added to the solution and the mixture was allowed to stand sitll in a cold place overnight. The formed precipitate was recovered by filtration and washed with acetone to obtain 2.2 g (the yield being 44%) of a dicyclohexylamine salt of 7-{D-(—)-α-[(2-oxo-3-(1,3-dithiolan-2-imino)-imidazolidin-1-yl)-carboxamido]-p-hydroxyphenylacetamido}-3-(1,3,4-thiadiazol-2-yl)-thiomethyl]-3-cephem-4-carboxylic acid in the form of a white crystalline powder having a melting point of 173° to 175° C. (decomposition).

IR (KBr) cm$^{-1}$: $\nu C=O$ 1780 (lactam)

'H-NMR(COCL$_3$+d$_6$-DMSO)δ: 1.17~2.39, 2.70~3.29(m, H of dicyclohexyl group), 3.57~3.66(m, 10H, CH$_2$×5), 4.49(broad-S, 2H, 3-CH$_2$), 4.85(d, J=4.88 Hz, 1H, 6-H), 5.65~5.77(m, 2H, 7-H, α-H), 6.70(d, J=8.30 Hz, 2H, 3',5'-phenyl nucleus), 7.24(d, J=8.30 Hz, 2H, 2', 6'-phenyl nucleus), 8.80~9.06(m, 2H, 2X-CONH—), 9.16(S, 1H, H of thiadiazole nucleus)

D$_2$O-Added δ: 1.17~2.12, 2.00~3.30(m, H of dicyclohexyl group), 3.57~3.68(m, 10H, CH$_2$×5), 4.51(broad-S, 2H, 3-CH$_2$), 4.85(d, J=4.88 Hz, 1H, 6-HO, 5.69(broad-S, 1H, 7-H, α-H), 6.71(d, J=8.30 Hz, 2H, 3', 5'-phenyl nucleus), 7.25(d, J=8.30 Hz, 2H, 2', 6'-phenyl nucleus), 9.15(S, 1H, H of thiadiazole nucleus)

EXAMPLE 18c

Preparation and purification of sodium 7-{D-(—)-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylate (hereinafter to as KI-6261)

According to the method described in Example 13d, 1.6 g (the yield being 80.4%) of a dimethylformamide adduct of sodium 7-{D-(—)-α-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-cephem-4-carboxylate was prepared in the form of a white crystalline powder having a melting point of 203° to 215° C. (decomposition) by using 2.2 g of a dicyclohexylamine salt of 7-{D-(—)-α-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylic acid.

IR (KBr) cm$^{-1}$: $\nu_{C=O}$ 1760 (lactam)

In the same manner as described above, 1.1 g (the yield being 75.8%) of sodium 7-{D-(—)-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylate was prepared in the form of a white crystalline powder having a melting point of 217° to 220° C. (decomposition) from 1.6 g of the dimethylformamide adduct of sodium 7-{D-(—)-α-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylate.

IR (KBr) cm$^{-1}$: $\nu_{C=O}$ 1760 (lactam)

In the same manner as described above, the above sodium salt was purified to obtain sodium 7-{D-(—)-α-[(2-oxo-3-(1,3-dithiolan-2-imino)-imidazolidin-1-yl)-carboxamido]-p-hydroxyphenylacetamido}-3-[(1,3,4-thiadiazol-2-yl)-thiomethyl]-3-cephem-4-carboxylate in the form of a white crystalline powder having a melting point of 214° to 216° C. (decomposition).

Elementary analysis values as C$_{25}$H$_{23}$N$_8$O$_7$S$_4$Na.H$_2$O: Calculated: C=40.10, H=3.37, N=14.96; Found: C=39.81, H=3.44, N=14.85

IR (KBr) cm$^{-1}$: $\nu_{C=O}$ 1760 (lactam) 1720, 1670 (amide)

'H-NMR(DMSO-d$_6$)δ: 3.62(10H, broad-S, CH$_2$×5), 4.47(2H, broad-S, 3-CH$_2$), 4.89(1H, d, J=4.88 Hz, 6-H), 5.56~5.44(2H, m, α-H, 7-H), 6.72(2H, d, J=8.30 Hz, 3', 5'-phenyl nucleus), 7.20(2H, d, J=8.30 Hz, 2',6'-phenyl nucleus), 8.77(1H, d, J=7.81 Hz, —CONH—), 9.25(1H, d, J=7.32 Hz, —CONH—), 9.50(1H, S, thiadiazol nucleus H)

D$_2$O-Added δ: 3.62(10H, broad-S, CH$_2$×5), 4.41(2H, broad-S, 3-CH$_2$), 4.86(1H, d, J=4.88 Hz, 6-H), 5.48 (1H, S, α-H), 5.55(1H, d, J=4.88 Hz, 7-H), 6.72(2H, d, J=8.30 Hz, 3', 5'-phenyl nucleus), 7.20(2H, d, J=8.30 Hz, 2',6'-phenyl nucleus), 9.47(1H, S, thiadiazole nucleus H)

$^{13}$C-NMR($^{12}$C-DMSO-d$_6$)δ: 26.51(t, 2-C), 35,99; 44.31 (t, imidazolidine nucleus-CH$_2$), 37.30(t, —CH$_2$—S), 37.68; 38.85(t, dithiolan nucleus-CH$_2$), 55.48(d, 6-C), 57.31(d, α-C), 57.96(d, 7-C), 114.35(S, 4-C), 115.26(d, 3',5'-phenyl nucleus), 127.74(d, 2',6'-phenyl nucleus), 128.26(S, 1-phenyl nucleus), 134.11(S, 3-C), 151.26(S, >N—CO—NH—), 153.86(d, 5'-thiadiazole nucleus), 155.03(S, C=N), 157.24 (S, 4'-phenyl nucleus), 162.83(S, 8-C), 164.12(S, —COONa), 166.33(S, 2'-thiadiazole nucleus), 170.75(S, imidazolidine nucleus C=O), 181.41(S, —CONH—)

EXAMPLE 19a

Preparation of 7-{D-(—)-α-[(2-oxo-3-(1,3-dithiolan-2-imino)-imidazolidin-1-yl)-carboxamido]-p-hydroxyphenylacetamido}-3-[(5-methyl-1,3,4-thiadia-2-yl)-thiomethyl]-3-cephem-4-carboxylic acid 7-{d-(—)-[(2-oxo-3-(1,3-dithiolan-2-imino)-imidazolidin-1-yl)-carboxamido]-p-hydroxyphenylacetamido}-3-[(5-methyl-1,3,4-thiadia-2-yl)-thiomethyl]-3-cephem-4-carboxylic acid was prepared in an amount of 3.26 g (the yield being 60%) in the form of a white powder having a melting point of 171° to 174° C. (decomposition) in the same manner as described in Example 13b except that 3.0 g of D-(—)-α-{[2-oxo-3-(1,3-dithiolan-2-imino)-imidazolidin-1-yl]-carboxamido}-p-hydroxyphenylacetic acid and 2.59 g of 7-amino-3-[(5-methyl-1,3,4-thiadiazol-2-yl)-thiomethyl]-3-cephem-4-carboxylic acid were used and trimethylchlorosilane and triethylamine were used in molar amounts two times the molar amounts used in Example 13b.

IR (KBr) cm$^{-1}$: $\nu_{C=O}$ 1780 (lactam)

EXAMPLE 19b

Preparation of dicyclohexylamine salt of 7-{D-(—)-α-[(2-oxo-3-(1,3-dithiolan-2-imino)-imidazolidin-1-yl)-carboxamido]-p-hydroxyphenylacetamido}-3-[(5-methyl-1,3,4-thiadiazol-2-yl)-thiomethyl]-3-cephem-4-carboxylic acid According to the method described in Example 17b, 2.3 g (the yield being 73.71%) of a dicyclohexylamine salt of 7-{D-(—)-α-[(2-oxo-3-(1,3-dithiolan-2-imino)-imidazolidin-1-yl)-carboxamido]-p-hydroxyphenylacetamido}-3-[(5-methyl-1,3,4-thiadiazol-2-yl)-thiomethyl]-3-cephem-4-carboxylic acid was prepared in the form of a white crystalline powder having a melting point of 173° to 174° C. (decomposition) by using 2.5 g of 7-{D-(—)-α-[(2-oxo-3-(1,3-dithiolan-2-imino)-imidazolidin-1-yl)carboxamido]-p-hydroxyphenylacetamido}-3-[(5-methyl-1,3,4-thiadiazol-2-yl)-thiomethyl]-3-cephem-4-carboxylic acid.

IR (KBr) cm$^{-1}$: $\nu$C=O 1780 (lactam)

$^1$H-NMR(COCL$_3$+d$_6$-DMSO)δ: 0.92~2.23; 2.86~3.22(m, H of dicyclohexyl group), 2.70(3H, S, —CH$_3$), 3.57~3.72(10H, m, CH$_2$×5), 4.43(2H, broad-S, -3-CH$_2$), 4.84(1H, d, J=4.88 Hz, 6-H), 5.36~5.97(2H, m, 7-H, α-H), 6.70(2H, d, J=8.30 Hz, 3',5'-phenyl nucleus H), 7.25(2H, d, J=8.30 Hz, 2',6'-phenyl nucleus H), 8.50~9.29(2H, m, 2×-CONH—)

D$_2$O-Added δ: 0.85~2.47; 2.89~3.14(m, H of dicyclohexyl group), 2.70(3H, S, —CH$_3$), 3.57~3.73(10H, m, CH$_2$×5), 4.43(2H, broad-S, 3-CH$_2$), 4.84(1H, d, J=4.88 Hz, 6-H), 5.68(1H, d, J=4.88 Hz, 7-H), 5.65(1H, S, α-H), 6.72(2H, d, J=8.30 Hz, 3',5'-phenyl group H), 7.25(2H, d, J=8.30 Hz, 2',6'-phenyl group H)

EXAMPLE 19c

Preparation and purification of sodium 7-{D-(—)-α-[(2-oxo-3-(1,3-dithiolan-2-imino)-imidazolidin-1-yl)-carboxamido]-p-hydroxyphenylacetamido}-3-[5-methyl(1,3,4-thiadiazol-2-yl)-thiomethyl]-3-cephem-4-carboxylate (hereinafter referred to as KI-6276)

According to the method described in Example 13d, 1.80 g (the yield being 90%) of a dimethylformamide adduct of sodium 7-{D-(—)-α-[(2-oxo-3-(1,3-dithiolan-2-imino)-imidazolidin-1-yl)-carboxamido]-p-hydroxyphenylacetamido}-3-[5-methyl-(1,3,4-thiadiazol-2-yl)-thiomethyl]-3-cephem-4-carboxylate was obtained in the form of a white powder having a melting point of 214° to 218° C. (decomposition) by using 2.3 g of a dicyclohexylamine salt of 7-{D-(—)-α-[(2-oxo-3-(1,3-dithiolan-2-imino)-imidazolidin-1-yl)-carboxamido]-p-hydroxy phenylacetamido}-3-[5-methyl-(1,3,4-thiadiazol-2-yl)-thiomethyl]-3-cephem-4-carboxylic acid.

IR (KBr) cm$^{-1}$: $\nu$C=O 1760 (lactam)

In the same manner as described above, 1.30 g (the yield being 79%) of sodium 7-{D-(—)-α-[(2-oxo-3-(1,3-dithiolan-2-imino)-imidazolidin-1-yl)-carboxamido]-p-hydroxyphenylacetamido}-3-[5-methyl-(1,3,4-thiadiazol-2-yl)-thiomethyl]-3-cephem-4-carboxylate was obtained in the form of a white crystalline powder having a melting point of 217° to 220° C. (decomposition) from 1.80 g of the dimethylformamide adduct of sodium 7-{D-(—)-α-[(2-oxo-3-(1,3-dithiolan-2-imino)-imidazolidin-1-yl)-carboxamido]-p-hydroxyphenylacetamido}-3-[5-methyl-(1,3,4-thiadiazol-2-yl)-thiomethyl]-3-cephem-4-carboxylate.

IR (KBr) cm$^{-1}$: $\nu$C=O 1760 (lactam)

In the same manner as described above, the above sodium salt was purified to obtain sodium 7-{D-(—)-α-[(2-oxo-3-(1,3-dithiolan-2-imino)-imidazolidin-1-yl)-carboxamido]-p-hydroxyphenylacetamido}-3-[5-methyl-(1,3,4-thiadiazol-2-yl)-thiomethyl]-3-cephem-4-carboxylate in the form of a white crystalline powder having a melting point of 218° to 221° C. (decomposition).

Elementary analysis values as C$_{26}$H$_{25}$O$_7$N$_8$S$_5$Na.2H$_2$O: Calculated: C=39.99, H=3.74, N=14.35, Found: C=40.16, H=3.53, N=14.41

IR(KBr) cm$^{-1}$: $\nu$C=O 1760 (lactam), 1720, 1670 (amide)

$^1$H-NMR(DMSO-d$_6$)δ: 2.66(3H, S, —CH$_3$), 3.62(10H, broad-S, 5×CH$_2$), 4.42(2H, broad-S, 3-CH$_2$), 4.87(1H, d, J=4.88 Hz, 6-H), 5.56~5.42(2H, m, α-H, 7-H), 6.71(2H, d, J=8.30 Hz, 3',5'-phenyl nucleus H), 7.19(2H, d, J=8.30 Hz, 2',6'-phenyl nucleus H), 8.77(1H, d, J=7.33 Hz, —CONH—), 9.25(1H, d, J=10.25 Hz, —CONH—)

D$_2$O-Added δ: 2.66(3H, S, —CH$_3$), 3.62(10H, broad-S, 5×CH$_2$), 4.37(2H, broad-S, 3-CH$_2$) 4.86(1H, d, J-4.88 Hz, 6H), 5.53(1H, d, J=4.88 Hz, 7-H), 5.48(1H, S, α-H), 6.73(2H, d, J=8.79 Hz, 3',5'-phenyl nucleus H), 7.22(2H, d, J=8.79 Hz, 2',6'-phenyl nucleus H)

$^{13}$C-NMR($^{12}$C-DMSO-d$_6$)δ: 15.20(q, —CH$_3$), 26.51(t, 2-C), 35.99; 44.31 (CH$_2$ of imidazolidine nucleus) 37.17(t, —CH$_2$S), 37.81; 38.85(t, CH$_2$ of dithiolan nucleus), 55.49(d, 6-C), 57.44(d, α-C) 57.96(d, 7-C), 114.87 (S, 4-C), 115.26(d, 3'5'-phenyl nucleus), 127.74(d, 2',6'-phenyl nucleus), 128.26 (S, 1'-phenyl nucleus), 133.72(S, 3-C), 151.26(S, >NCONH), 155.03(S, C=N), 162.95(S, 8-C), 164.38(S, -100Na) 165.42(S, 5'-thiadiazole nucleus), 165.94(S, 2'-thiadiazole nucleus), 170.75(S, imidazoline nucleus C=O), 181.53(S, —CONH—)

EXAMPLE 19d

Preparation of 7-{D-(—)-α-[(2-oxo-3-(1,3-dithiolan-2-imino)-imidazolidin-1-yl)-carboxamido]-p-acetoxyphenylacetamido}-3-[5-methyl-(1,3,4-thiadiazol-2-yl)-thiomethyl]-3-cephem-4-carboxylic acid To a suspension of 2.0 g of the compound obtained in Example 19a in 25 ml of water was added 2.7 ml of 1 N sodium hydroxide to form a solution having a pH value of 8.0, and 0.622 g of acetic anhydride was dropped to the solution with stirring under ice cooling over a period of 40 minutes while maintaining the pH value of 7 to 8 by addition of 1N sodium hydroxide. The mixture was stirred under ice cooling for 1.5 hours while maintaining the pH value at 7 to 8. The reaction mixture was filtered and the pH value was adjusted to 2 by 2 N HCL. The precipitated crystal was recovered by filtration, washed with water and dried in a vacuum desiccator to obtain 1.912 g (the yield being 90.3%) of the intended compound. The melting point was 160° to 163° C. (decomposition).

IR (KBr) cm$^{-1}$: $\nu$C=O 1760 (lactam), 1720, 1680(ester, amide)

NHR(d$_6$-DMSO)δ: 2.27(3H, S,

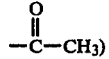

2.69(3H, S, CH$_3$ of thiazole nucleus), 3.63(10H, broad-S, CH$_2$×5), 4.20 4.50(2H, m, 3-CH$_2$), 5.05(1H, d, J=6 Hz, 6-H), 5.50~5.90(2H, m, 7-H, α-H), 7.17, 7.53(4H, d, J=8 Hz, C₆H₄—) 9.02(1H, d, J=8 Hz, —COHN—), 9.55(1H, d, J=8 Hz, —CONH—)

EXAMPLE 19e

Preparation of phthalidyl 7-{D-(—)-α-[(2-oxo-3-(1,3-dithiolan-2-imino)-imidazolidin-1-yl)-carboxamido]-p-hydroxyphenylacetamido}-3-[5-methyl-(1,3,4-thiadiazol-2-yl)-thiomethyl]-3-cephem-4-carboxylate In 10 ml of dimethylformamide was dissolved 1.49 g (2 millimoles) of sodium 7-{D-(—)-α-[(2-oxo-3-(1,3-dithiolan-2-imino)-imidazolidin-1-yl)-carboxamido]-p-hydroxyphenyl-acetamido}-3-[5-methyl-(1,3,4-thiadiazol-2-yl)-thiomethyl]-3-cephem-4-carboxylate at room temperature, and 0.014 g of potassium carbonate was added to the solution and the mixture was maintained at 0° to 5° C. with stirring. Then, 0.47 g (2.2 millimoles) of phthalidyl bromide was added to the mixture and stirring was conducted at the same temperature for 2.5 hours. The reaction mixture was poured into 500 ml of ice water, and the precipitate was recovered by filtration, washed with water and dried in vacuo in a desiccator by phosphorus pentoxide to obtain 1.248 g (the yield being 72.98%) of a crude crystal of phthalidyl 7-{D-(—)-α-[(2-oxo-3-(1,3-dithiolan-2-imino)-imidazolidin-1-yl)-carboxamido]-p-hydroxyphenylacetamido}-3-[5-methyl-(1,3,4-thiadiazol-2-yl)-thiomethyl]-3-cephem-4-carboxylate. The crude product was purified by silica gel column chromatography (developing solvent: methanol/chloroform =1/9) to obtain 0.495 g (the yield being 28.94%) of a pure product having a melting point of 163° C. (decomposition).

IR (KBr) cm⁻¹: 1780(VS), 1720(VS), 1675(S), 1510(S), 1390(S), 1258(S), 970(S)

¹H-NMR(DMSO-d₆)δ: 2.65(S, 3H, —CH₃), 3.19~3.88(m, 12H, CH₂×6), 4.99(d, J=6.0 Hz, 1H, 6-H), 5.33~5.60(m, 2H, α-H, 7-H), 6.68, 7.15(d, 4H, J=8.0 Hz, C₆H₄—), 7.33~8.06(m, 5H, H of phthalidyl group), 8.70(d, J=8.0 Hz, 1H, —CONH), 9.25(d, J=8.0 Hz, 1H, —CONH)

What is claimed is:

1. A novel cephalosporin represented by the following formula:

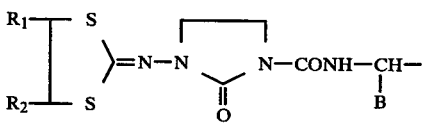
(I)

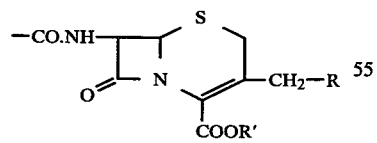

wherein R is hydrogen, acyloxy of formula R₄COO—, in which R₄ is alkyl of 1 to 4 carbon atoms; carbamoyloxy, a pyridinium radical of formula

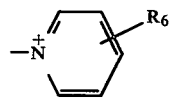

in which R₆ is hydrogen, alkyl having 1 to 4 carbon atoms, carboxy, lower alkoxy, carbamoyl, halogen or sulfamoyl or a group —S—Het in which Het is

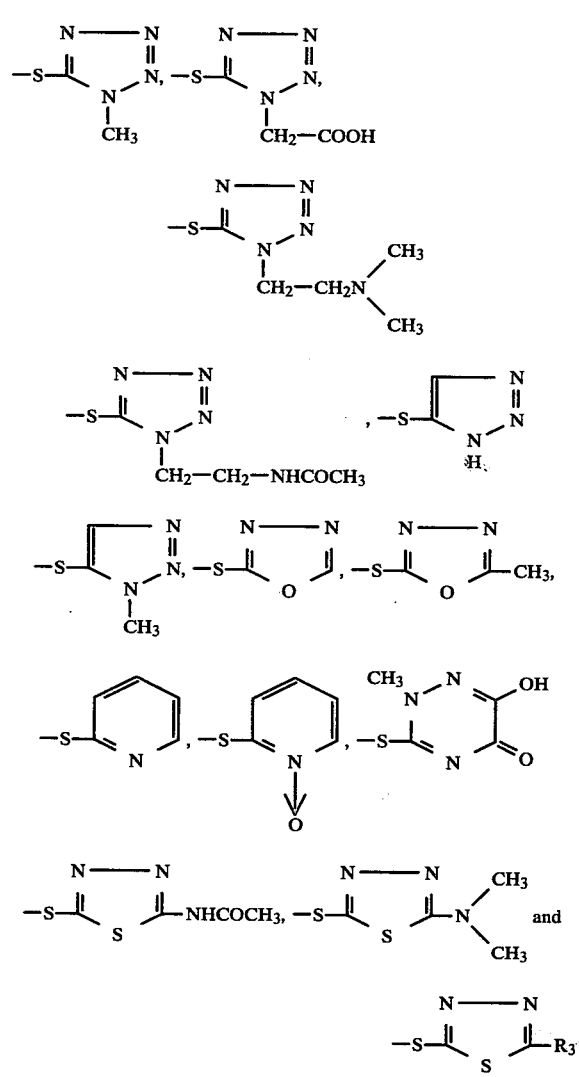

in which R₃ is hydrogen or alkyl having 1 to 4 carbon atoms, R' is hydrogen, alkali metal, an organic amine or an ester moiety, R₁ and R₂ are the same or different and are hydrogen or lower alkyl and B stands for a 1,4-cyclohexadienyl group, a group

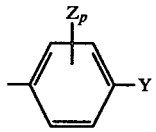

in which Y is hydrogen, —OH or

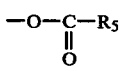

in which R₅ is alkyl having 1 to 5 carbon atoms, or alkoxy having 1 to 4 carbon atoms, Z is hydrogen or halogen and p is an integer of 1 or 2, a furan group or a thiophene group.

2. A novel cephalosporin as set forth in claim 1, wherein the compound represented by the formula (I) is 7-{D-(—)-α-[(2-oxo-3-(1,3-dithiolan-2-imino)-imidazolidin-1-yl)carboxamido]-(1,4-cyclohexadien-1-yl)-acetamido}-3-methyl-3-cephem-4-carboxylic acid.

3. A novel cephalosporin as set forth in claim 1, wherein the compound represented by the formula (I) is 7-{D-(—)-α-[(2-oxo-3-(1,3-dithiolan-2-imino)-imidazolidin-1-yl)carboxamido]-4-hydroxyphenylacetamido}-3-[(1,2,3-triazol-5-yl)-thiomethyl]-3-cephem-4-carboxylic acid.

4. A novel cephalosporin as set forth in claim 1, wherein the compound represented by the formula (I) is 7-{D-(—)-α-[(2-oxo-3-(4-methyl-1,3-dithiolan-2-imino)-imidazolidin-1-yl)-carboxamido]-phenylacetamido}-3-acetoxymethyl-3-cephem-4-carboxylic acid.

5. A novel cephalosporin as set forth in claim 1, wherein the compound represented by the formula (I) is sodium 7-{D-(—)-α-[(2-oxo-3-(1,3-dithiolan-2-imino)-imidazolin-1-yl)-carboxamido]-phenylacetamido}-3-acetoxymethyl-3-cephem-4-carboxylate.

6. A novel cephalosporin as set forth in claim 1, wherein the compound represented by the formula (I) is sodium 7-{D-(—)-α-[(2-oxo-3-(1,3-dithiolan-2-imino)-imidazolidin-1-yl)-carboxamido]-phenylacetamido}-3-[(1-methyl-1,2,3,4-tetrazol-5-yl)-thiomethyl]-3-cephem-4-carboxylate.

7. A novel cephalosprin as set forth in claim 1, wherein the compound represented by the formula (I) is sodium 7-{D-(—)-α-[(2-oxo-3-(1,3-dithiolan-2-imino)-imidazolidin-1-yl)-carboxamido]-4-hydroxyphenylacetamido}-3-(1-methyl-1,2,3,4-tetrazol-5-yl)-thiomethyl]-3-cephem-4-carboxylate.

8. A novel cephalosporin derivative as set forth in claim 1, wherein the compound represented by the general formula (I) is 7-{D-(—)-α-[(2-oxo-3-(1,3-dithiolan-2-imino)-imidazolidin-1-yl)-carboxamido]-4-acetoxyphenylacetamido}-3-[(1-methyl-1,2,3,4-tetrazol-5-yl)-thiomethyl]-3-cephem-4-carboxylic acid.

9. A novel cephalosporin as set forth in claim 1, wherein the compound represented by the formula (I) is sodium 7-{D-(—)-α-[(2-oxo-3-(1,3-dithiolan-2-imino)-imidazolidin-1-yl)-carboxamido]-phenylacetamido}-3-[(1,3,4-thiadiazol-2-yl)-thiomethyl]-3-cephem-4-carboxylate.

10. A novel cephalosporin as set forth in claim 1, wherein the compound represented by the formula (I) is 7-{D-(—)-α-[(2-oxo-3-(1,3-dithiolan-2-imino)-imidazolidin-1-yl)-carboxamido]-phenylacetamido}-3-[5-methyl(1,3,4-thiadiazol-2-yl)-thiomethyl]-3-cephem-4-carboxylic acid.

11. A novel cephalosporin as set forth in claim 1, wherein the compound represented by the formula (I) is 7-{D-(—)-α-[(2-oxo-3-(4-methyl-1,3-dithiolan-2-imino)-imidazolidin-1-yl)-carboxamido]-phenylacetamido}-3-[5-methyl-(1,3,4-thiadiazol-2-yl)-thiomethyl]-3-cephem-4-carboxylic acid.

* * * * *